(12) United States Patent
Russo et al.

(10) Patent No.: US 10,426,703 B2
(45) Date of Patent: Oct. 1, 2019

(54) VIAL ADAPTERS

(71) Applicant: UNL Holdings LLC, New York, NY (US)

(72) Inventors: Robert Scott Russo, Eagleville, PA (US); Jeffrey M. Johnson, San Diego, CA (US); Christopher C. Rafferty, Raworth (AU); Tod H. Brenner, Pequea, PA (US); Gautam N. Shetty, Lancaster, PA (US)

(73) Assignee: UNL Holdings LLC, New York, NY (US)

( * ) Notice: Subject to any disclaimer, the term of this patent is extended or adjusted under 35 U.S.C. 154(b) by 831 days.

(21) Appl. No.: 14/436,389

(22) PCT Filed: Dec. 5, 2013

(86) PCT No.: PCT/US2013/073283
§ 371 (c)(1),
(2) Date: Apr. 16, 2015

(87) PCT Pub. No.: WO2014/099395
PCT Pub. Date: Jun. 26, 2014

(65) Prior Publication Data
US 2015/0265500 A1    Sep. 24, 2015

Related U.S. Application Data

(60) Provisional application No. 61/738,151, filed on Dec. 17, 2012.

(51) Int. Cl.
*A61M 5/32* (2006.01)
*A61J 1/20* (2006.01)

(52) U.S. Cl.
CPC ............. *A61J 1/2096* (2013.01); *A61J 1/201* (2015.05); *A61J 1/2065* (2015.05); *A61M 5/322* (2013.01); *A61J 1/2055* (2015.05)

(58) Field of Classification Search
CPC ........ A61J 1/201; A61J 1/2096; A61J 1/2065; A61M 2005/3231; A61M 5/322;
(Continued)

(56) References Cited

U.S. PATENT DOCUMENTS

2010/0179506 A1   7/2010   Shemesh et al.
2010/0204679 A1   8/2010   Denenburg
(Continued)

FOREIGN PATENT DOCUMENTS

CN   101918074 A   12/2010
CN   101969914 A    2/2011
(Continued)

OTHER PUBLICATIONS

International Search Report from International PCT Application No. PCT/US2013/073283 (dated Mar. 13, 2014).

*Primary Examiner* — Ariana Zimbouski
(74) *Attorney, Agent, or Firm* — Hamilton, Brook, Smith & Reynolds, P.C.

(57) ABSTRACT

A vial adapter is provided for interconnecting a vial having a closure and a fluid delivery device such as a safety syringe. The vial adapter comprises an adapter housing having a base, a shroud extending or projecting from the base and a cannula extending or projecting from the base for penetrating a rubber seal on the vial closure to thereby establish fluid communication between the vial and the vial adapter. The shroud may comprise a plurality of latitudinal slits or windows within each of which resides a flexion arm connected to the shroud, each flexion arm capable of engaging and/or retaining vial closures of any of a variety of different sizes. The vial adapter may comprise a conduit tip in fluid communication with the cannula to allow transfer of fluid to or from the safety syringe while also preventing inadvertent activation of a safety syringe needle retraction mechanism.

18 Claims, 22 Drawing Sheets

(58) Field of Classification Search
CPC .. A61M 5/3234; A61M 5/3232; A61M 5/502; A61M 2005/3241; A61M 2005/5033
See application file for complete search history.

(56) References Cited

U.S. PATENT DOCUMENTS

2011/0022023 A1   1/2011  Weitzel et al.
2011/0160701 A1*  6/2011  Wyatt ................... A61J 1/2096
                                          604/519

FOREIGN PATENT DOCUMENTS

EP          2252250 B1   5/2012
EP          2190518 B1   1/2016
WO   WO 2011/057335 A1   5/2011

* cited by examiner

VIAL ADAPTERS

TECHNICAL FIELD

THIS INVENTION relates to connectors of the type used in the handling and administration of parenterally-administered fluids. More particularly, this invention relates to a vial adapter having a sharp cannula for piercing a vial closure, a shroud protecting an operator from inadvertent puncture by the sharp cannula and enabling removable connection to a vial, and a connector opposite the sharp cannula for connection to a device for fluid flow.

BACKGROUND

Access ports for injecting fluid into or removing fluid from a system, such as a drug vial, are well known and widely used. Conventional injection sites in drug vials generally involve a pierceable rubber stopper formed of an elastomeric material such as butyl rubber or the like, placed in the opening of the vial. A closure, typically formed of metal, is crimped over the rubber stopper and the flange of the vial to positively hold the stopper in place in the opening of the vial. The closure has an outer size, known as a "finish size." The closure also has an opening, or access port, through which the stopper and the vial opening may be accessed. A sharp cannula is inserted into the access port piercing the rubber stopper to position the distal, open end of the cannula past the rubber stopper to make fluid connection with the interior of the vial. Such a configuration is useful when reconstituting a powder (i.e., adding a diluent or a liquid substance to a powder to make a solution, emulsion, or the like). A growing number of drug therapies are preferably stored and/or transported in a powder form and, accordingly, require reconstitution or mixing into a liquid substance prior to injection and delivery into a patient.

Adapters have been found useful in that they can adapt the sharpened cannula that is placed into fluid communication with the vial to the connection device of another fluid container or fluid delivery device such as a syringe. For example, the adapter may include a female Luer fitting opposite the sharpened cannula to receive the nozzle of a syringe. Luer connection systems are a standard way of attaching syringes, catheters, hubbed needles, IV tubes, and the like to each other. Luer connections consist of conical/tubular male and female interlocking components slightly tapered to hold together better. Luer connections can either be a "luer slip", which are luer connections with a simple pressure or twist fit, or luer connections can be a "luer lock", which can have an additional outer rim of threading allowing them to be more secure. The "adapter" therefore adapts the vial to the syringe, or adapts the sharpened cannula to the Luer-shaped nozzle of the syringe.

It has also been found useful to provide a means to attach or anchor the adapter to the vial to hold it in place while fluid communication between the vial and another device proceeds so that inadvertent disengagement of the adapter from the vial does not occur. For example, the adapter may have two arms that engage the neck or flange of the vial and hold the adapter in place on the vial. Other means include a shroud that fits around the outside of the vial closure and snaps onto the vial closure under the crimped retaining cap thereby grasping the vial neck flange and the underside of the closure.

However, some of the existing adapters available today suffer from various shortcomings. For example, most adapters are designed to function only on a single vial closure finish size. These adapters do not securely attach to vial closures with diameters smaller or larger than vial closure finish sizes they are primarily molded to fit. They are therefore not usable on vials of other sizes. In addition, some vial adapters do not adequately protect an operator from inadvertent puncture of the operator's skin by the sharpened cannula of the adapter. The shroud or vial engagement device does not extend completely over the sharpened cannula, thus exposing operators to possible puncture.

Accompanying this limitation of functioning with only a single size of vial, a further consideration is the expense to hospitals or other medical facilities caused by having to stock numerous types and sizes of adapters. Vials of many flange sizes and closure sizes are available and are frequently found in medical care facilities. Typically a hospital must stock a variety of adapters to be assured of having the correct adapter available that will properly interconnect with the multiple vial closures that exist. If a hospital must maintain a stock of adapters for each possible size of closure, a logistical problem as well as increased expense can result. Two common sizes of vial closures are 13 mm vial closures and 20 mm vial closures. Reducing the number of adapters that must be stocked in a hospital can significantly lessen the problems with stocking the correct sizes and can reduce expenses.

Certain vial adapters exist that can accommodate multiple sizes of vial closure finishes. Such adapters generally utilize an adapter skirt having a plurality of longitudinal slits. The skirt may have a flare configuration to accept vials of multiple sizes, with the longitudinal slits creating flexible arms. When the cannula is inserted through a cap of a vial, interior aspects of the flexible arms are configured to engage with the vial beneath the cap of the vial. Therefore, the adapter is retained in position on the vial, and because the arms are flexible, the adapter can be retained on vials having different vial closure diameters. However, a practical way to accommodate a range of vial finish sizes, including the large vial finish sizes which are increasingly common in industry, is needed. Hence, those concerned with the development of medical adapters have recognized the need for a single adapter that is usable with vials of different sizes.

SUMMARY

In a broad form, the invention is directed to a vial adapter for interconnecting a vial and a fluid delivery device. In one form, the vial adapter is for interconnecting vials having a variety of different closure sizes to said fluid delivery device. In a further or alternative form, the vial adapter is for interconnecting a vial and a fluid delivery device in the form of a safety syringe, wherein the vial adapter minimizes the risk of inadvertently activating a safety mechanism of the safety syringe.

In an aspect, the invention provides a vial adapter for interconnecting a vial having a closure having a seal and a fluid delivery device, said vial adapter comprising an adapter housing having a base, a shroud extending or projecting from the base and a cannula extending or projecting from the base for penetrating said seal to thereby establish fluid communication between the vial and the vial adapter, wherein the shroud comprises one or a plurality of latitudinal apertures within at least one of which resides a flexion arm connected at one end to the shroud, each flexion arm capable of engaging and/or retaining the vial closure.

The latitudinal apertures may be slits, windows, slots, cutouts or other apertures that extend laterally within the shroud. Suitably, each flexion arm is a lateral flexion arm.

The length and/or number of the latitudinal apertures and/or flexion arms is preferably selected for engaging a vial closure within a broad range of sizes (e.g., diameters). Conveniently, the length of each of the flexion arms is such that when the adapter engages a relatively smaller diameter vial closure, at least one of the flexion arms contacts and deforms to engage the smaller vial closure. Typically, the flexion arms are capable of deformation. Suitably, each of the flexion arms is capable of elastic deformation or plastic deformation. In at least one embodiment, the flexion arms comprise a narrowed segment at which the gross deformation takes place. Advantageously, the flexion arms may deflect laterally under elastic deformation as a result of a force directed axially through a center line of the vial adapter. For example, such an arrangement may allow the flexion arms to engage (e.g., snap under) a retaining cap surrounding a seal in the vial closure. Each flexion arm may further comprise a gripping aspect that facilitates engaging and/or retaining the vial in fluid communication with the vial closure.

In one embodiment, the base of the adapter housing comprises an outer surface and an inner surface. Suitably, at least part of the cannula extends or projects from the inner surface. Conveniently, in at least one embodiment the shroud extends from the base to surround a sharp tip of the cannula to thereby protect an operator of the vial adapter from inadvertent puncture by the tip of the cannula.

One or more embodiments of the vial adapter may further include a distal flare extending or projecting from the shroud. In use, the distal flare extends or projects outwardly from a distal end of the shroud. Said flare may be useful in aiding a user to attach the vial adapter to a vial closure. Suitably, the flare is dimensioned so as to be readily gripped or otherwise handled by the user.

In another embodiment, the vial adapter further comprises a collar. Suitably the collar is located at a proximal portion of the adapter housing. Typically, the collar facilitates connection of a syringe to the vial adapter by being adapted to receive the end of a barrel of a syringe for connection to the vial adapter. This prevents the syringe from wobbling while the user is depressing or withdrawing the syringe plunger. According to this embodiment, optionally the angles of the interior surface of the vial adapter may be selected to promote an audible "snap" when the vial adapter is connected to the vial.

In at least one embodiment, a connector extends or projects from the adapter housing, preferably from the base. In use, the connector extends or projects proximally from the base. The connector may comprise a Luer-slip, Luer-lock or any other connection type used in the art to connect the vial adapter to another fluid vial, a container or to a fluid delivery device. The connector may contain the female or the male components of the connection type, including the Luer-type connection, such that it is capable of interfacing and/or engaging the corresponding syringe or other fluid delivery device. The connector may comprise an interior aperture or pass-through permitting fluid flow to and/or from a fluid delivery device through the cannula of the vial adapter to the vial closure. In at least one embodiment, the connector may further comprise a gasket, washer, O-ring, seal, or other similar component, such as an elastomeric gasket or O-ring. Such gaskets may assist, for example, in providing a tight connection between corresponding components of the connector of the vial adapter and the fluid delivery device and/or vial. The gaskets may similarly be utilized to minimize "dead space", i.e., space within a component that may fill with fluid, to ensure that substantially all of the desired fluid transfer occurs between the components and devices.

As will be evident from the foregoing, in some embodiments the vial adapter of the present invention may be used to interconnect a vial and a fluid delivery device, such as a syringe, for fluid transfer between the vial and the fluid delivery device. Preferably, the vial adapter is utilized to connect between a vial and a safety syringe. Safety syringes are syringes which have integrated needle safety mechanisms to prevent accidental needle sticks and undesirable reuse of the syringe. By way of example, the safety syringes may be those which utilize the needle safety mechanisms as described in International Publication WO2006/119570, International Publication WO2006/108243, International Publication WO2009/003234, International Publication WO2011/057335 and/or International Publication WO2011/075760, although without limitation thereto. In some embodiments, the safety syringes may be "retractable" syringes that utilize a needle retraction safety mechanism which activates at the end of plunger travel or depression (i.e., at the end of fluid delivery). In some particular embodiments, the retractable needle may be replaceable, such as described for example in International Publication WO2011/057335.

Advantageously, to prevent premature activation of the needle retraction safety mechanism of the safety syringe, one or more embodiments of the vial adapter of the present invention may further comprise a conduit tip. Typically, the conduit tip projects from the connector. Preferably, in use the conduit tip projects proximally from the connector. The conduit tip may be attachable to the connector or may be integrally formed or otherwise preformed with the connector. The conduit tip may comprise a protrusion which prevents or inhibits activation of a safety mechanism of the safety syringe. The conduit tip may have one or more internal apertures that permit fluid flow through the conduit tip. Typically, at least part of the cannula is in fluid communication with the conduit tip. This arrangement allows fluid communication between the vial, the cannula and the conduit tip.

Accordingly, another aspect of the invention provides a vial adapter for interconnecting a vial comprising a closure having a seal and a safety syringe, said vial adapter comprising an adapter housing having a base, a shroud extending or projecting from the base which is capable of releasably engaging and/or retaining the vial closure, a cannula extending or projecting from the base for penetrating said seal to thereby establish fluid communication between the vial and the vial adapter and a conduit tip which prevents or inhibits activation of a safety mechanism of the safety syringe.

Typically, the conduit tip projects or extends from the connector. In use, the conduit tip projects or extends proximally from the connector. The conduit tip may be attachable to the connector or may be integrally formed or unitary with the connector. The conduit tip suitably comprises a protrusion which prevents or inhibits activation of a safety mechanism of the safety syringe. Preferably, the safety syringe is a retractable syringe that comprises a needle refraction mechanism, as hereinbefore described.

The conduit tip may have one or more internal apertures that permit fluid flow through the conduit tip. Typically, at least part of the cannula is in fluid communication with the conduit tip. This arrangement allows fluid communication between the vial, the cannula and the conduit tip.

In at least one embodiment, the shroud further comprises one or a plurality of latitudinal apertures within at least one of which resides a flexion arm connected at one end to the shroud, as hereinbefore described. Suitably, flexion arms are capable of engaging and/or retaining the vial adapter on the vial closure. Preferably, the length and/or number of the latitudinal slits and/or flexion arms is capable of releasably engaging and/or retaining a vial closure within a broad range of sizes (e.g., diameters). Each flexion arm may comprise a gripping aspect, as hereinbefore described.

In an alternative embodiment, the shroud comprises one or a plurality of longitudinal slits, wherein longitudinal arms respectively reside between adjacent slits, each connected at one end to the shroud. Suitably, the longitudinal arms are capable of engaging and/or retaining the vial adapter on the vial closure. Preferably, the longitudinal arms are deformable. The longitudinal arms may be capable of elastic or plastic deformation.

In yet another aspect, the invention provides a method of transferring fluid from a vial comprising a closure having a seal to a fluid delivery device, said method including the step of releasably connecting a vial adapter to the closure of the vial and to a fluid delivery device by fitting lateral arms of the vial adapter to the closure so that the vial adapter is in fluid communication with said fluid delivery device.

Suitably, the method further includes the step of transferring fluid between the vial and said fluid delivery device. Suitably, the vial adapter is as hereinbefore described according to the aforementioned aspects. Preferably, the fluid delivery device is a safety syringe such as hereinbefore described.

A further aspect of the invention provides a method of transferring fluid from a vial comprising a closure having a seal to a fluid delivery device comprising a safety mechanism, said method including the step of inserting a conduit tip of a vial adapter into said fluid delivery device to so that the vial adapter is in fluid communication with said fluid delivery device.

Suitably, the method further includes the step of transferring fluid between the vial to said fluid delivery device. Suitably, insertion of the conduit tip of the vial adapter into said fluid delivery device avoids or prevents activation of the safety mechanism. Suitably, the vial adapter is as hereinbefore described according to any of the aforementioned aspects comprising said conduit tip. Preferably, the fluid delivery device is a safety syringe comprising a needle retraction mechanism, such as hereinbefore described.

In a yet further aspect, the invention provides a kit comprising at least one vial adapter of any of the aforementioned aspects and at least one fluid delivery device, or individual components thereof. In one embodiment, the fluid delivery device is a safety syringe. In one particular embodiment, the safety syringe comprises a barrel, plunger and a retractable needle. Preferably, according to this embodiment the kit provides a plurality of retractable needles, each of a different size or gauge. Optionally, the retractable needle (or each retractable needle) is a replaceable retractable needle.

Other features and advantages of the present invention will become apparent from the following detailed description of preferred embodiments which, taken in conjunction with the accompanying drawings, illustrate by way, of example the principles of the invention.

Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

BRIEF DESCRIPTION OF THE DRAWINGS

The following non-limiting embodiments of the invention are described herein with reference to the following drawings, wherein.

DETAILED DESCRIPTION

As will be described further below, embodiments of the present invention may include one or more additional components which may be considered standard components in the industry of medical devices. The components, and embodiments containing such components, are within the contemplation of the present invention and are to be understood as falling within the breadth and scope of the present invention. Reference to "proximal" or "proximally" in respect of a recited element means that in operation or use, the element projects, extends, is located or oriented towards or closer to an operator or user. Reference to "distal" or "distally" in respect of a recited element means that in operation or use, the element projects, extends is oriented or located away from an operator or user.

Embodiments of vial adapter 100 of the invention will be described in the context of a syringe, such as a safety syringe having a safety mechanism in the form of a retractable needle (i.e. a retractable syringe). It will be appreciated that the vial adapter may facilitate fluid transfer from a vial to the syringe to thereby reconstitute a powdered, dried, desiccated, dehydrated or otherwise solid substance in the syringe or may facilitate transfer of fluid from the syringe to the vial to thereby reconstitute a powdered, dried, desiccated, dehydrated or otherwise solid substance in the vial. In the latter case, the reconstituted fluid substance is then drawn back into the syringe for subsequent delivery, as is well understood in the art.

Figure 1A:
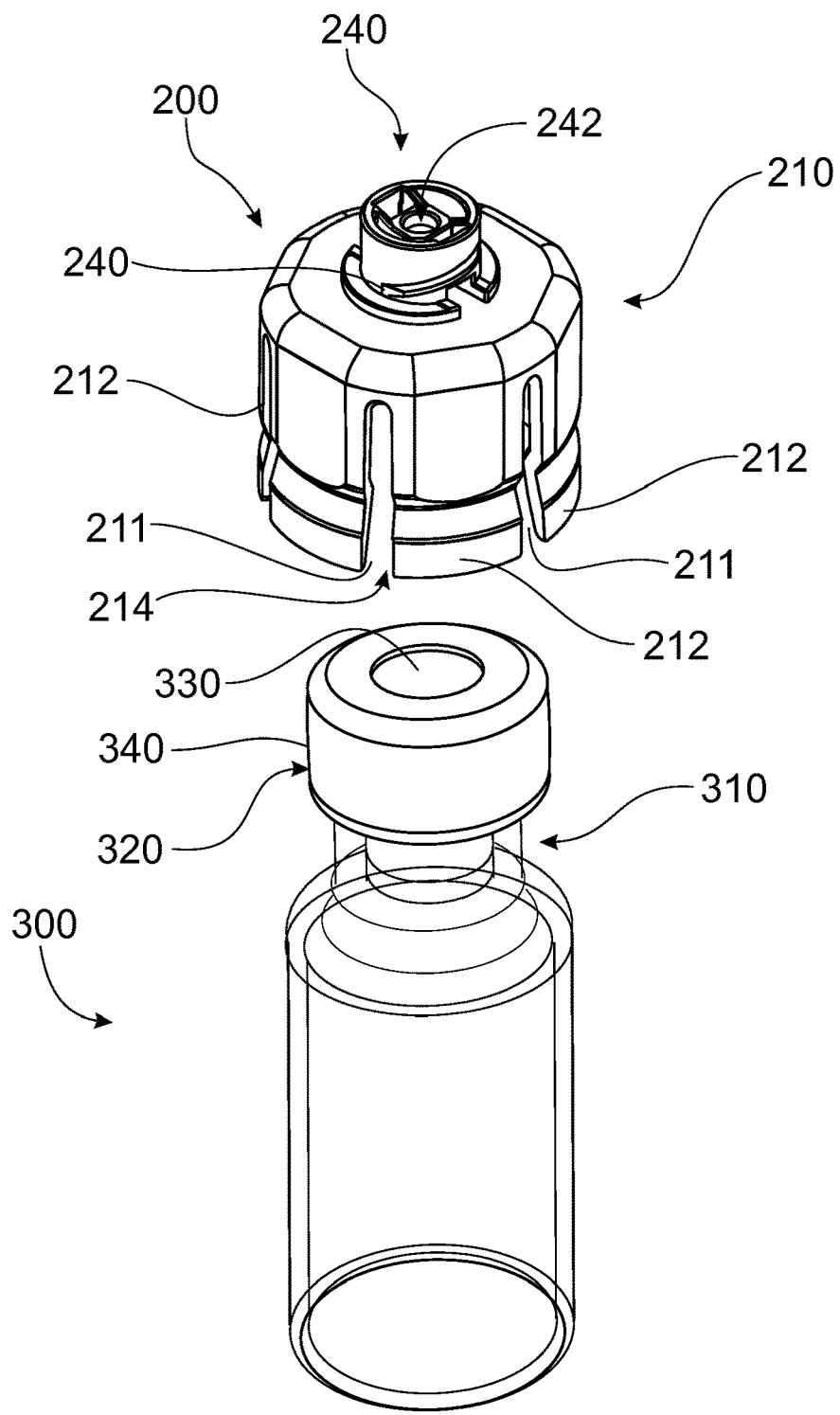
FIG. 1A is an isometric view of a prior art vial adapter and a vial.
Figure 1B:
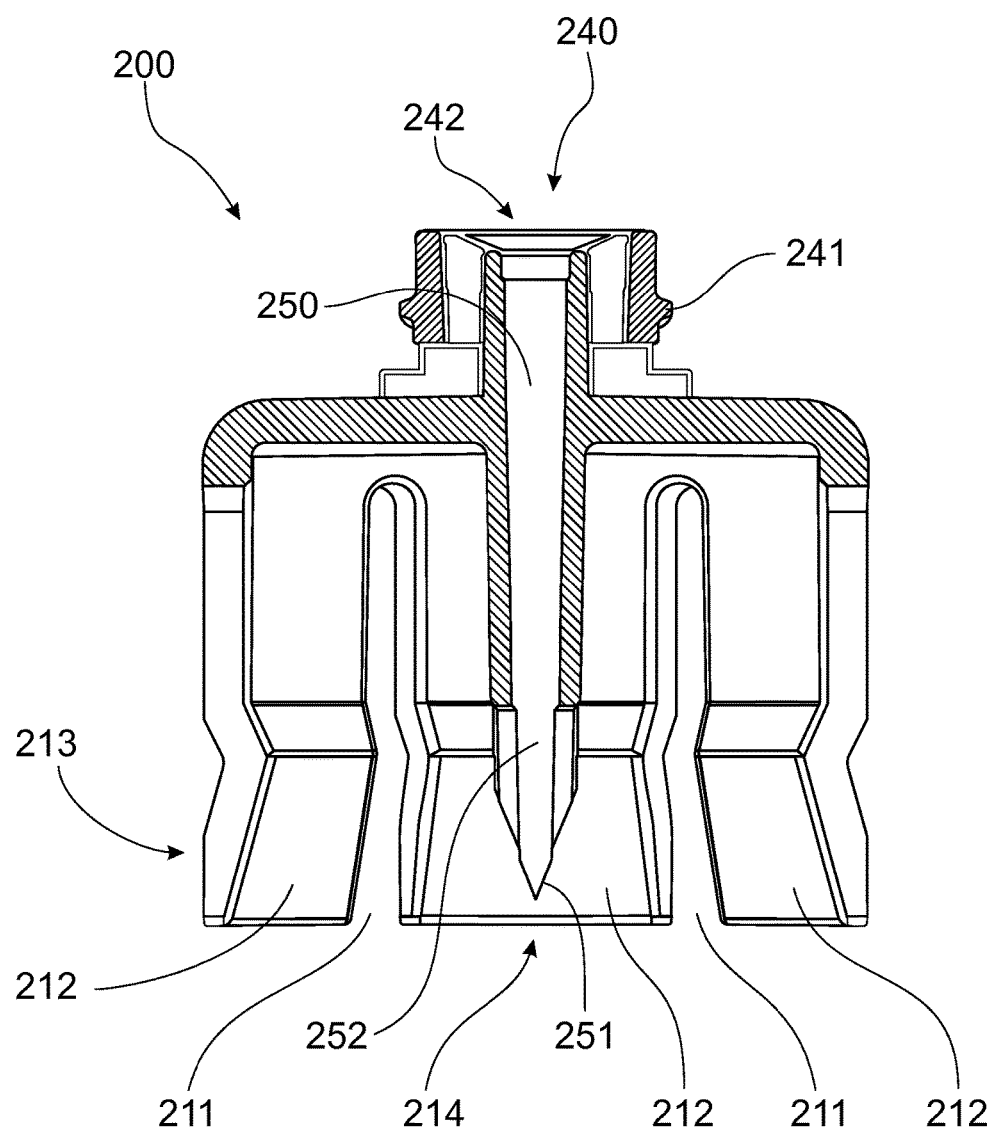
FIG. 1B is a sectional view of a prior art vial adapter and a vial.

For initial reference, FIG. 1A shows an isometric view of an example of a prior art vial adapter 200 and vial 300. FIG. 1B shows a sectional view of prior art vial adapter 200. Vial 300 comprises container 310 closure 320 to which is fitted rubber seal 330 and crimped metal retainer 340. Vial adapter has housing 210 with longitudinal slits 211 and longitudinal arms 212 for connection to vial closure 310, the longitudinal slits 211 and longitudinal arms 212 forming a generally "flower petal" shaped vial adapter 200. This configuration defines cavity 314 that fits over vial closure 320, enabling and longitudinal arms 212 to engage crimped metal retainer 340 fitted to vial closure 310. Cannula 230 has sharp tip 231 capable of piercing rubber seal 320 of vial 300. Connector 240 has bore 242 capable of fluid communication with internal aperture 232 of cannula 230. Connector 240 comprises luer 241 which is connectable to a syringe having a compatible luer connection (not shown) to thereby establish fluid communication between vial 300, vial adapter 200 and syringe (not shown). Vial adapter 200 may be convenient for vial closures 320 of one particular size but not for others. It is also noted that longitudinal slits 211 and longitudinal arms 212 extend into, and completely through, skirt portion 213, thereby complicating manufacture. Additionally or alternatively, vial adapter 200 does not function to prevent premature activation of safety mechanisms that may be part of a syringe or other fluid delivery device to which vial adapter 200 may be connected.

Figure 2A:
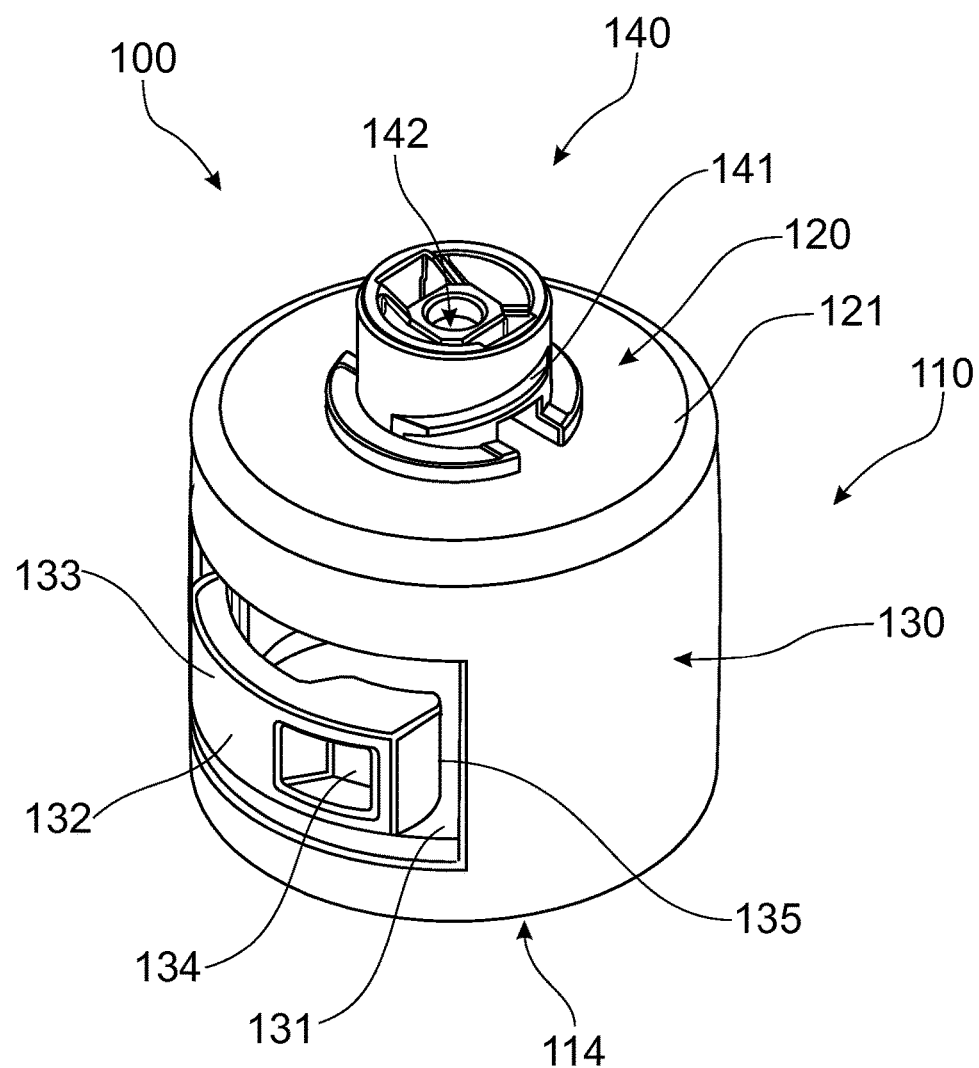
FIG. 2A is an isometric view of a vial adapter according to an embodiment of the present invention.
Figure 2B:
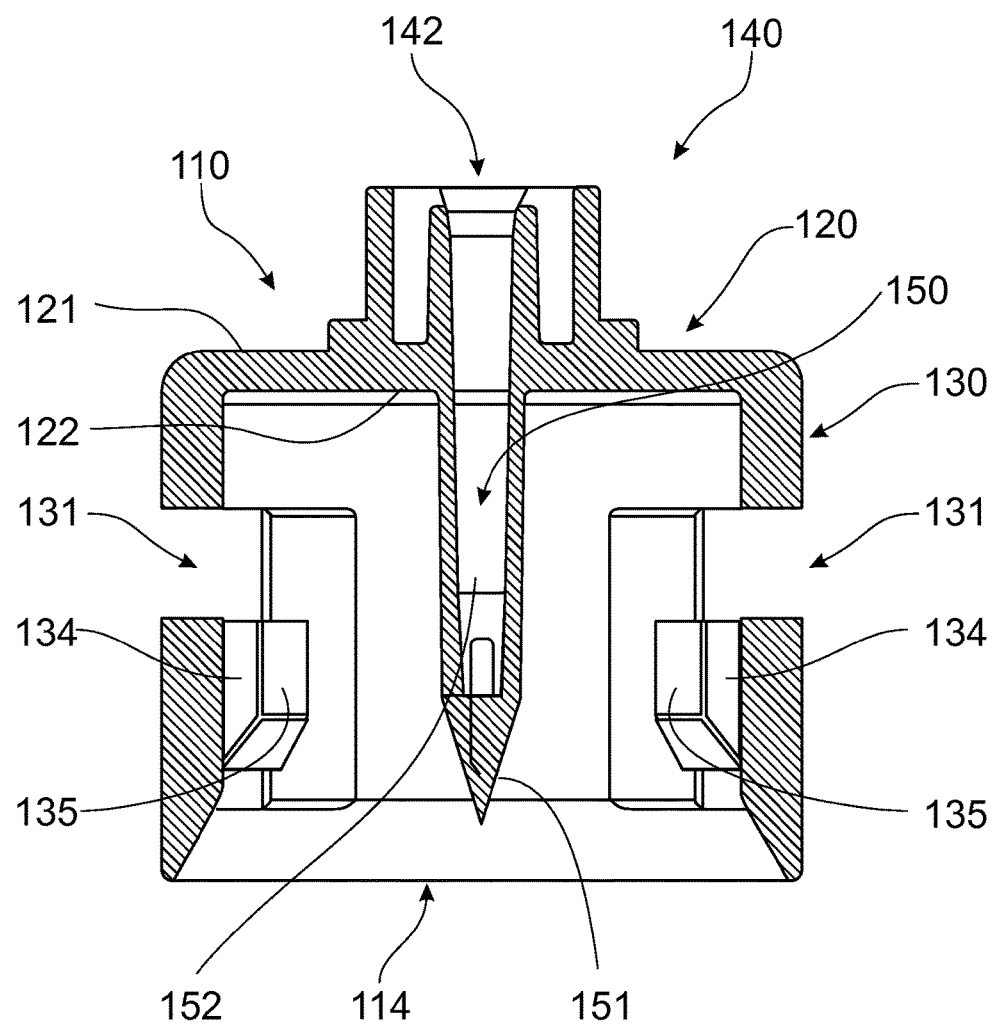
FIG. 2B is a cross-sectional side view of the vial adapter shown in FIG. 2A.

Certain embodiments of the present invention provide vial adapter 100 which is capable of connecting to vial closures 320 of various diameters and sizes. One such embodiment of vial adapter 100 of the present invention is shown in FIG. 2A and has a relatively uniform external profile (compared to that described in FIG. 1) while enabling connection to vial closures 320 of various sizes and diameters. FIG. 2B is a cross-sectional side view of vial adapter 100. Vial adapter 100 has housing 110 having base 120 and shroud 130 extending or projecting distally therefrom comprising latitudinal slits or windows 131 having respective flexion arms 132 which are permitted to deform, flex, or otherwise distort (at least temporarily and/or partially). Flexion arms 132 are respectively hingedly connected to shroud 130 through end 133. Flexion arms 132 respectively further comprise gripping aspect 134 which comprises gripping surface 135 (best seen in FIG. 2B) which can engage a vial closure, such as by the gripping crimped metal retainer shown in FIG. 1A. The number of latitudinal slits or windows 131 and respective flexion arms 132 may be readily varied, but in this embodiment two latitudinal slits or windows 131 and respective flexion arms 132 are provided. Additionally, while the latitudinal slits or windows 131 and respective flexion arms 132 are shown in a counter-clockwise configuration, they may readily be manufactured and utilized in a clockwise configuration while remaining within the embodiments of the present invention. Furthermore, as shown in FIGS. 3A-3D, the latitudinal slits or windows 131 and respective flexion arms 132 are substantially latitudinal in function but may have a diagonal aspect or configuration for, for example, aesthetics. Connector 140 extends or projects proximally from outer surface 121 of base 120 and comprises bore 142 and luer 141 whereby a fluid delivery device such as a syringe having a compatible luer connection (shown, for example, in FIGS. 3A-3B, and 10) may be connected to connector 140.

Cannula 150 comprises distal portion 153 which projects or extends substantially axially from inner surface 121 of base 120 and resides within internal cavity 114 of shroud housing 110. Cannula 150 further comprises internal aperture or pass-through 152 in fluid communication with bore 142 of connector to permit fluid flow between a vial closure and connector 140. It will be appreciated that shroud 130 extends from base 120 to surround a sharp tip of the cannula to thereby protect an operator of the vial adapter from inadvertent puncture by sharp tip 151 of cannula 150.

Figure 3A:
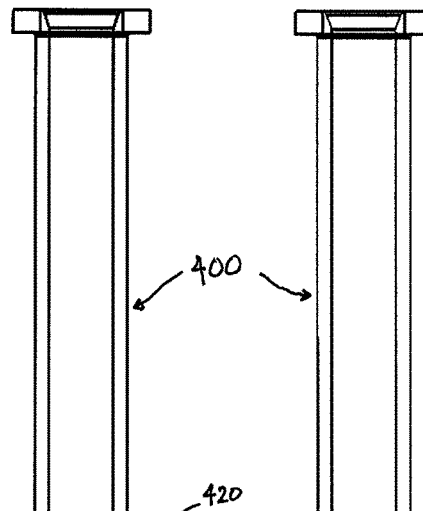
FIG. 3A is a side view of a vial adapter, according to at least one embodiment of the present invention, when connected to vial on one end and a syringe having a luer-type connection on the other end.
Figure 3B:
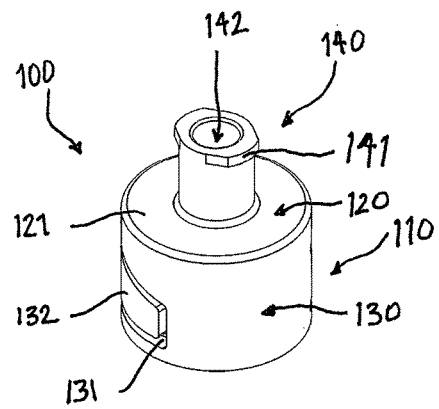
FIG. 3B is a cross-sectional side view of the vial adapter, vial, and syringe having a luer-type connection shown in FIG. 3A.

The connector may comprise a Luer-slip, Luer-lock or any other connection type used in the art to connect the vial adapter to another fluid vial, a container or to a fluid delivery device. The connector may contain the female or the male components of the connection type, including the Luer-type connection, such that it is capable of interfacing and/or engaging the corresponding syringe or other fluid delivery device. The connector may comprise an interior aperture or pass-through permitting fluid flow to and/or from a fluid delivery device through the cannula of the vial adapter to the vial closure. FIG. 3A is a side view of a vial adapter, according to at least one embodiment of the present invention, when connected to vial on one end and a syringe having a luer-type connection on the other end. FIG. 3B is a cross-sectional side view of the embodiment shown in FIG. 3A. As shown, the connector 140 of vial adapter 100 contains a luer-type connection. The connector 140 may be utilized to connect vial adapter 100 to a fluid delivery device, such as syringe 400. The vial adapter 100 may also be connected to vial 300, to facilitate fluid transfer between vial 300 and syringe 400, or vice versa.

Figure 3C:
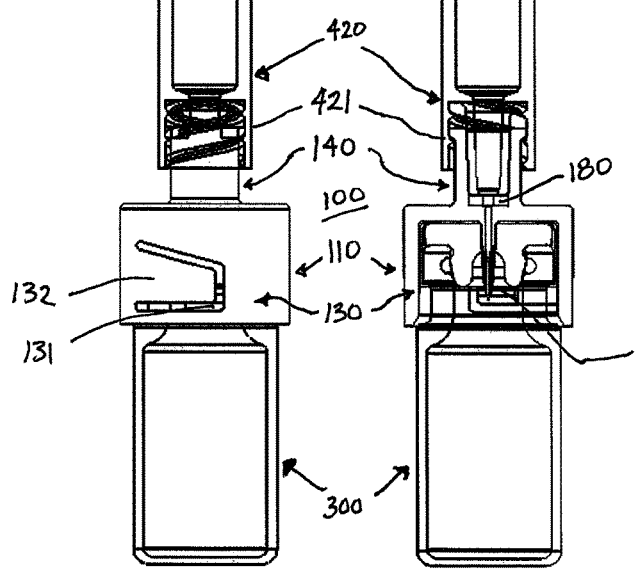
FIG. 3C is an isometric view of the vial adapter shown in FIG. 3A.
Figure 3D:
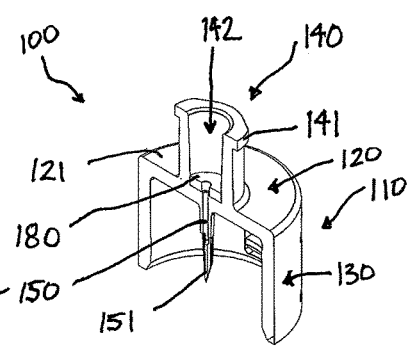
FIG. 3D is an cross-sectional isometric view of the vial adapter shown in FIG. 3C.

FIG. 3C provides an isometric view of the vial adapter shown in FIG. 3A, while FIG. 3D provides a cross-sectional isometric view of the vial adapter shown in FIG. 3C. In at least one embodiment, as shown in FIGS. 3C-3D, the connector may further comprise a gasket 180. Gasket 180 may be a gasket, washer, O-ring, seal, or other similar component, such as an elastomeric gasket or O-ring. Such gaskets may assist, for example, in providing a tight connection between corresponding components of the connector 140 of vial adapter 100 and the fluid delivery device 400 and/or vial 300. The gaskets may similarly be utilized to minimize "dead space", i.e., space within a component that may fill with fluid, to ensure that substantially all of the desired fluid transfer occurs between the components and devices.

Figure 4A:
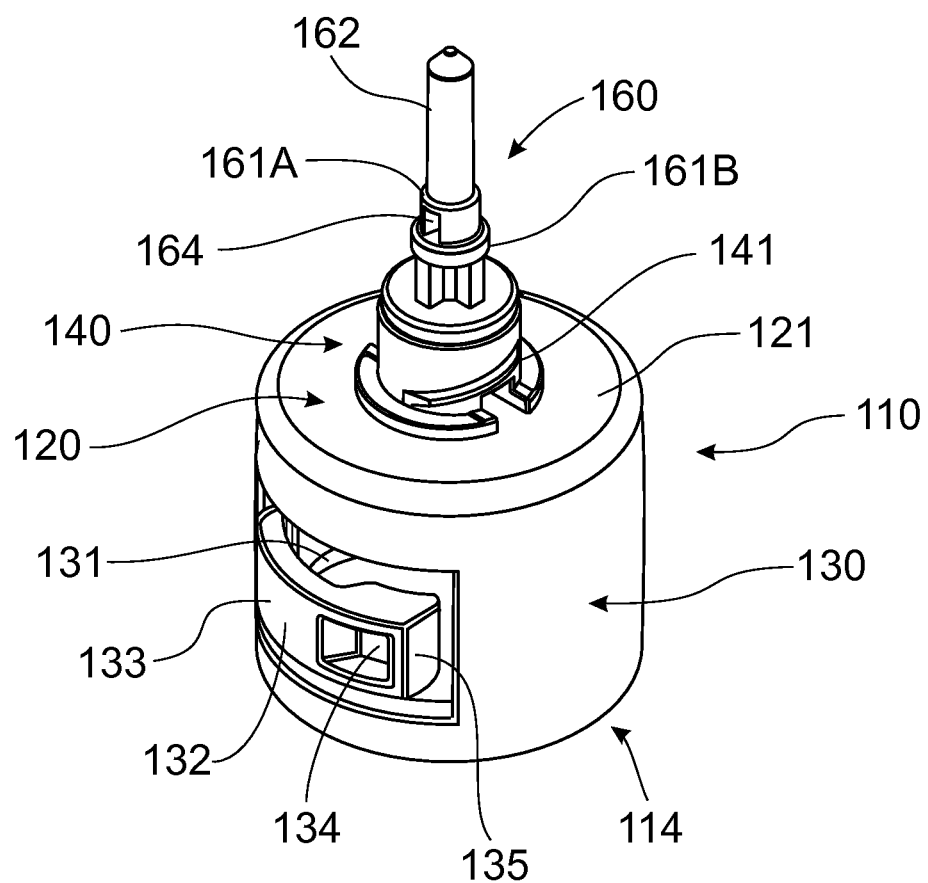
FIG. 4A is an isometric view of a vial adapter comprising a conduit tip.
Figure 4B:
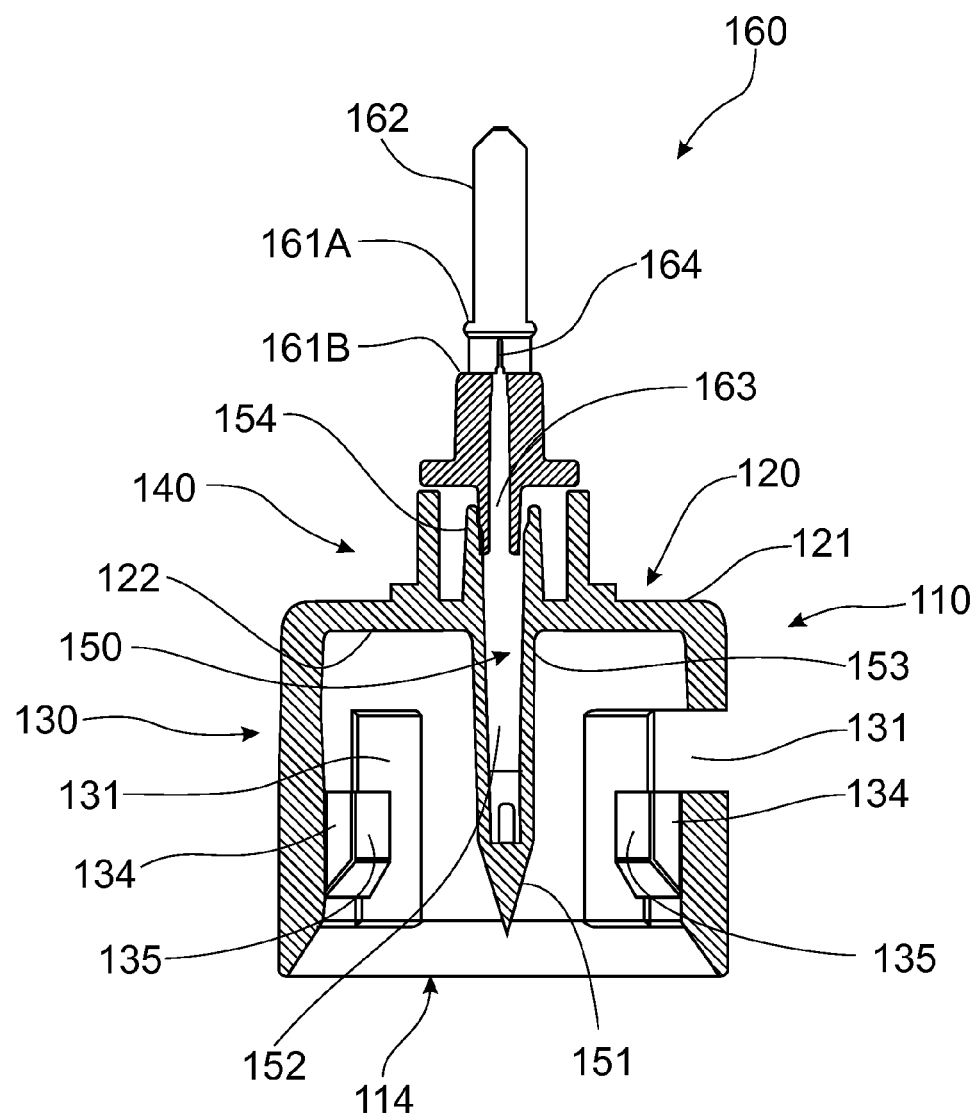
FIG. 4B is a cross-sectional side view of the vial adapter shown in FIG. 4A.

FIG. 4A is an isometric view and FIG. 4B is a sectional view of an embodiment of vial adapter 100 similar to that shown in FIGS. 2A and 2B, but further comprising conduit tip 160 which permits fluid flow between a fluid delivery device, such as a safety syringe, and a vial closure with an at least reduced risk of premature activation of the syringe safety mechanism (e.g., needle refraction mechanism). Conduit tip 160 has a generally stepped configuration comprising shoulders 161A, B and projection 162. Internal bore 163 is in fluid communication with internal aperture or pass-through 151 of cannula 150 and comprises outlet port 164.

Figure 5A:
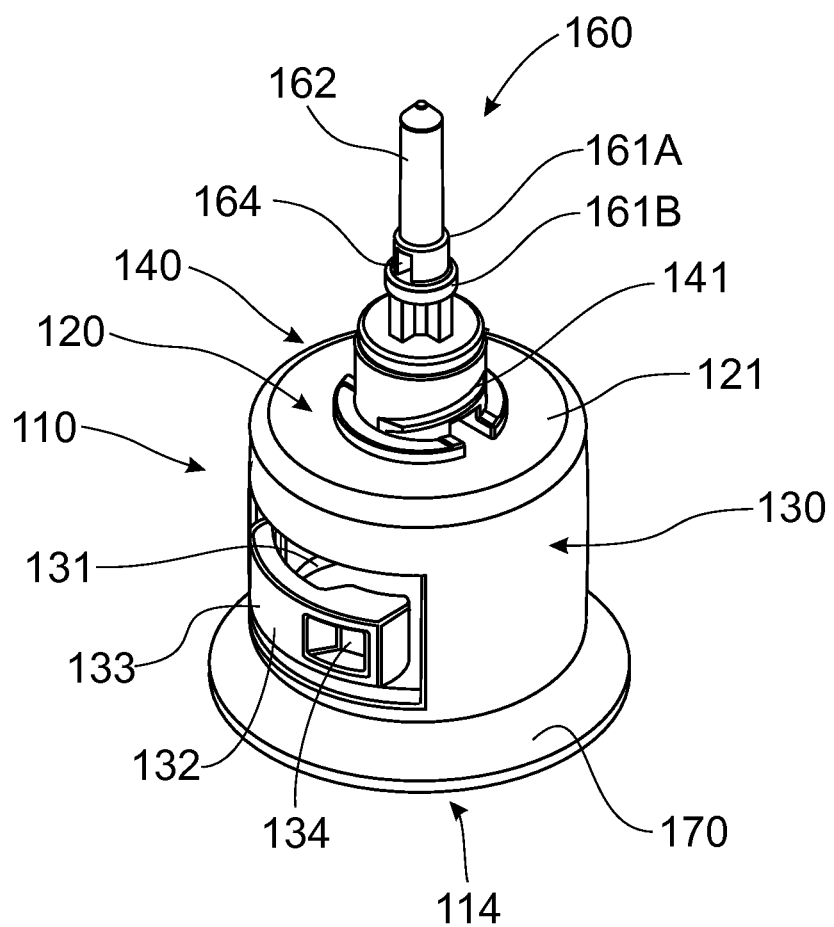
FIG. 5A is an isometric view of a vial adapter having a distal flare.
Figure 5B:
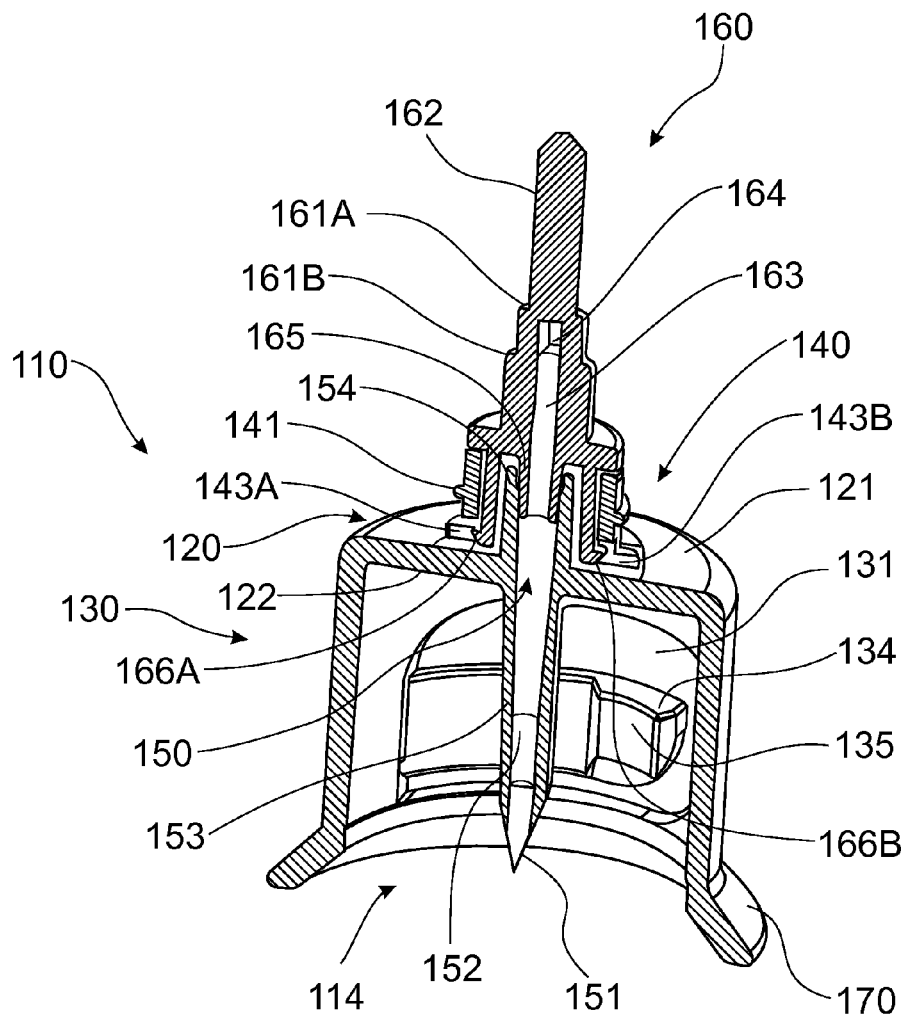
FIG. 5B is a sectional view of the vial adapter of FIG. 5B.

FIG. 5A is an isometric view of vial adapter 100 and FIG. 4B is a sectional view of vial adapter 100 according to an embodiment having distal flare 170. Distal flare 170 may be useful in aiding a user in attaching vial adapter 100 to a vial closure. In the embodiment shown in FIG. 5B, conduit tip 160 may be fitted to connector 140 by way of deformable hook arms 166A, B engaging recesses 143A, B in connector 140. Fluid communication between cannula 150 and conduit tip 160 is established by end portion 165 of conduit tip 160 fitting into internal aperture or pass-through 151 in proximal portion 154 of cannula 150 so that bore 163 is in fluid communication with internal aperture or pass-through 151 of cannula 150. In an alternative embodiment, connector 140 and conduit tip 160 may be an integrally-formed or otherwise pre-formed structure.

Figure 6:
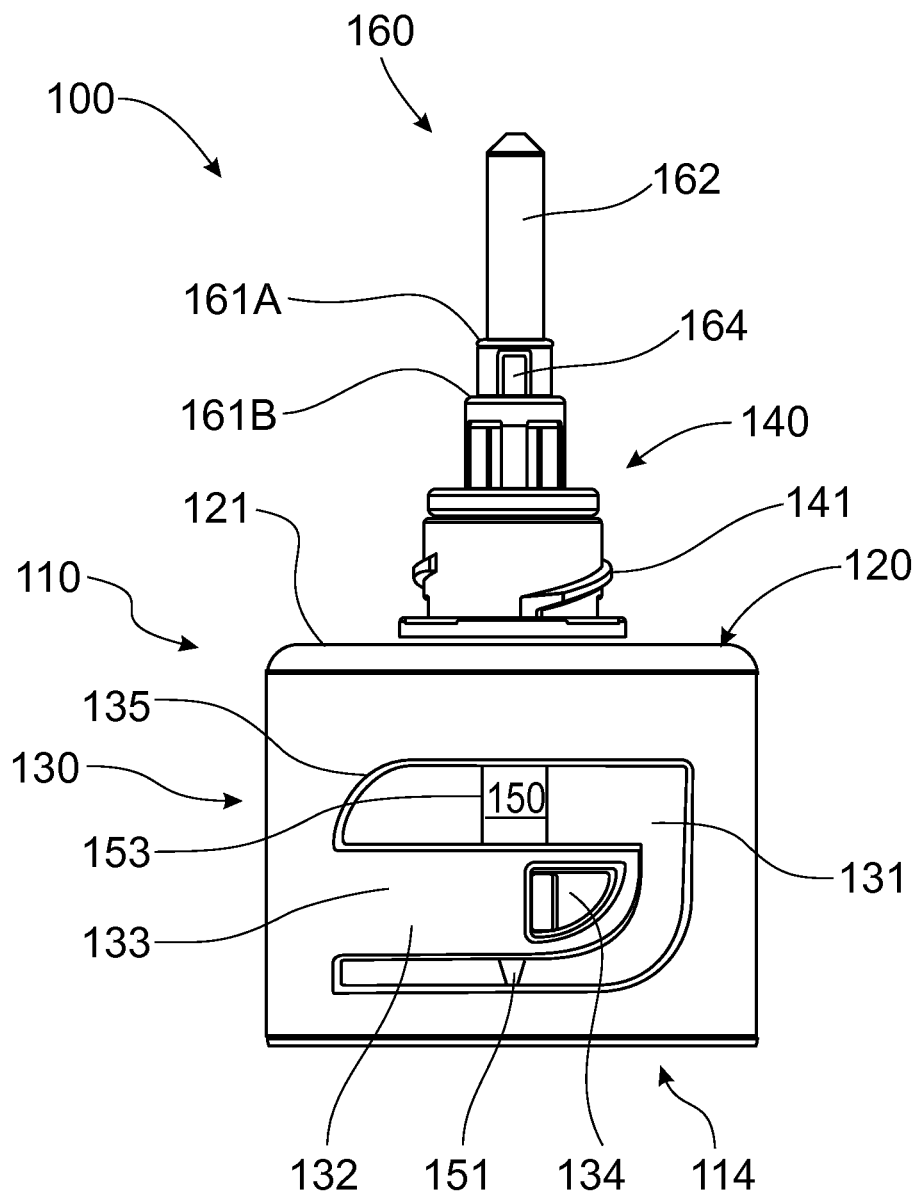
FIG. 6 is a side view of another embodiment of a vial adapter.

Latitudinal slits or windows 131 and flexion arms 132, may take a number of shapes and/or configurations while remaining within the scope and contemplation of the present invention. For example, FIG. 6 is a side view of another embodiment of vial adapter 100, having a more rounded latitudinal slit or window 131 by curvilinear edge 135.

Figure 7:
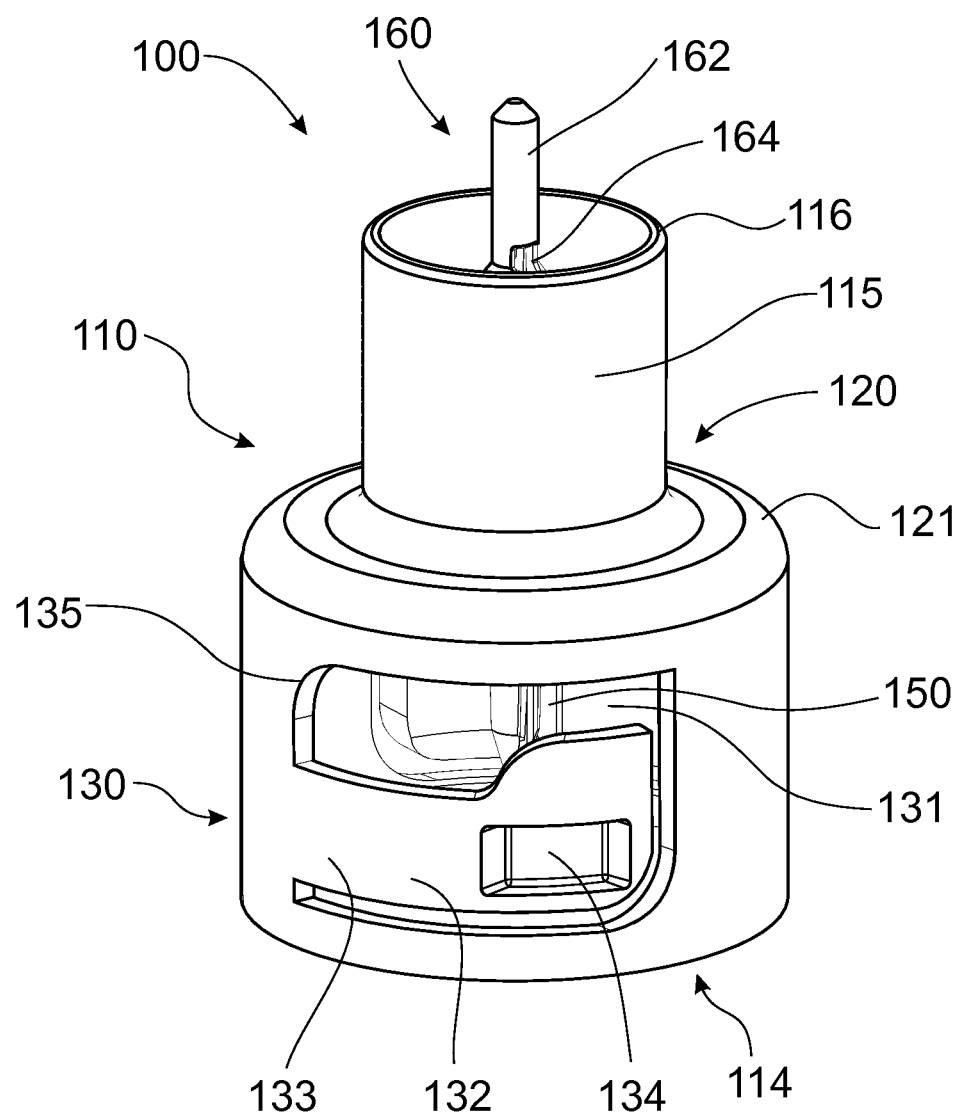
FIG. 7 is an isometric view of a vial adapter comprising a collar.

FIG. 7 shows an embodiment of vial adapter 100 wherein housing 110 comprises collar 115 which is substantially annular and encloses connector 140. Collar 115 comprises lip 116 and is integrally formed with, and projects from, outer surface 121 of base 120 and may be suitably dimensioned to facilitate connection of a syringe to vial adapter 100 by being adapted to receive the end or nose of a barrel of the syringe for connection to vial adapter 100. This may facilitate a better connection between the syringe and the vial adapter and/or prevent a syringe from wobbling while the user is depressing or withdrawing the syringe plunger. An additional variation in this embodiment is that the angles of the interior surface of the vial adapter, for example at surfaces 134 and/or 135, may be adjusted to promote an audible "snap" when vial adapter 100 is connected to vial 300.

Figure 8:
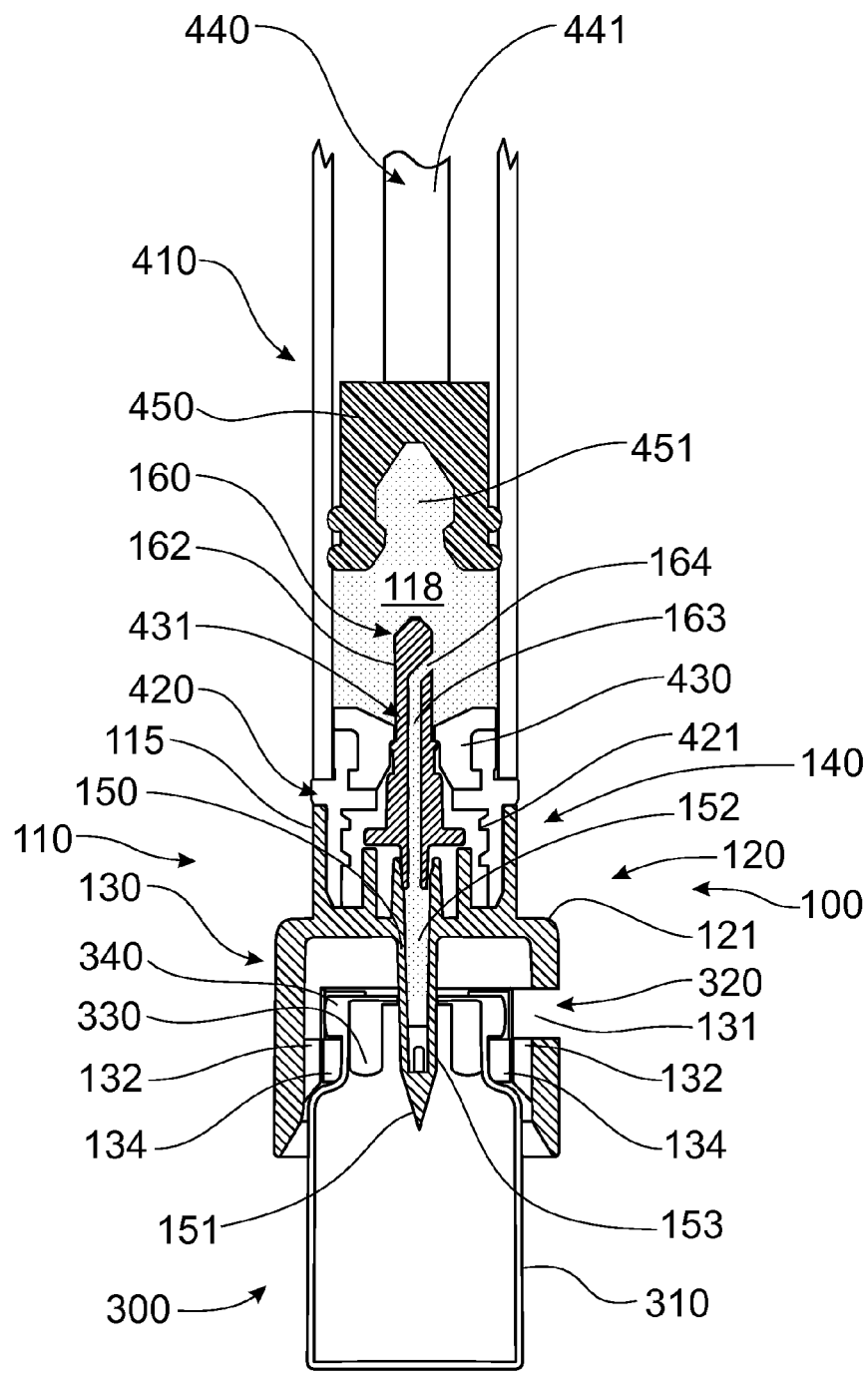
FIG. 8 is a cross-sectional view of a vial adapter in fluid communication with a vial and a syringe.

FIG. 8 shows an exemplary embodiment of vial adapter 100 in fluid communication with vial 300 and retractable syringe 400. Vial 300 comprises container 310 closure 320, to which rubber seal 330 and crimped metal retainer 340 are fitted. In this embodiment, retractable syringe 400 is of a type described in WO2011/057335 having a replaceable needle assembly. It will be appreciated that this embodiment of retractable syringe 400 is for illustrative purposes only and that vial adapter 100 can be used with a variety of different syringes such as hereinbefore described. In FIG. 8, tip 151 of cannula 150 penetrates rubber seal 330 of vial 300 and lateral flexion arms 131 engage vial closure by, for example, clampingly engaging crimped metal retainer. Gripping aspects 134 fit under crimped metal retainer 340. Syringe 400 comprises barrel 410, barrel adapter 420 comprising female thread 421, needle seal 430 having needle aperture 431 and plunger 440 having plunger member 441 and plunger seal 450 that comprises needle-engaging member 451. Although not shown, plunger 440 is of the type which comprises an internally-housed, compressed spring, whereby a release mechanism allows spring decompression to drive needle retraction. In FIG. 8, the replaceable needle assembly (not shown) has been screw-threadedly removed from female thread 421 of barrel adapter 420. Conduit tip 160 penetrates aperture 431 in needle seal 430 which normally accommodates the retractable needle body (not shown) and prevents depression or travel of plunger 440 to a point where the release mechanism is activated and spring decompression can occur (such as fully described in WO2011/057335). Accordingly, fluid 118 can be transferred from syringe 400 to vial 300 or vice versa by way of bore 163 of conduit tip 160 and internal aperture or pass-through 151 of cannula 150, to thereby reconstitute a solid substance (not shown) in the vial or the syringe. Once reconstitution has occurred, the mixed fluid is drawn back into the syringe 400. Vial adapter 300 and syringe 400 are disconnected and the replaceable needle assembly is screwed into syringe barrel adapter 420. Additionally or alternatively, fluid 118 can be transferred from syringe 400 to vial 300 or vice versa by way of bore 163 of conduit tip 160 and internal aperture or pass-through 151 of cannula 150, to thereby mix with a liquid substance (not shown) in the vial or the syringe. Once mixing has occurred, the mixed fluid is drawn back into the syringe 400. Vial adapter 300 and syringe 400 are disconnected and the replaceable needle assembly is screwed into syringe barrel adapter 420. In the embodiment shown in FIG. 8, cannula 150 and conduit tip 160 are separate components. Alternatively, it is contemplated that cannula 150 and conduit tip 160 could be a single, unitary or integrally-formed structure.

Figure 9A:
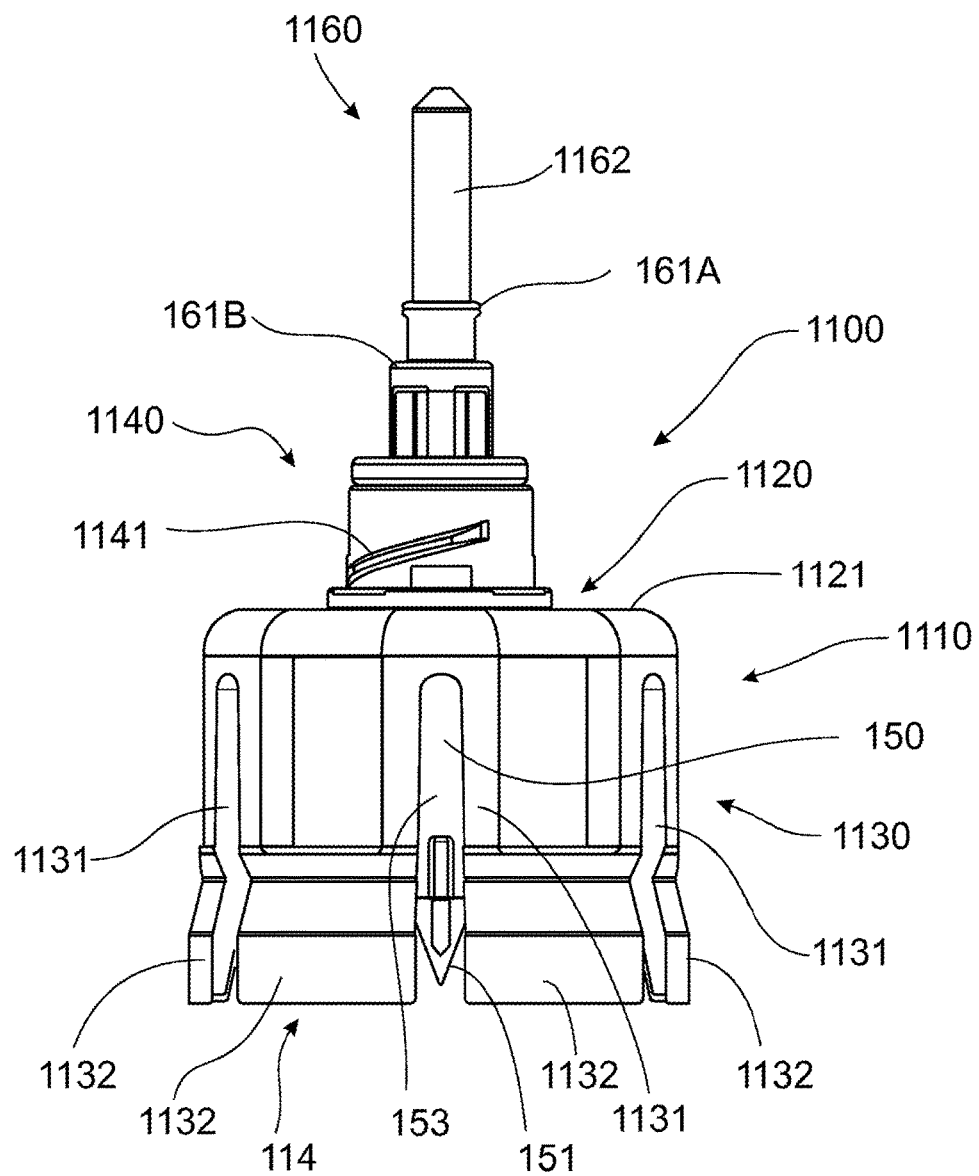
FIG. 9A is an isometric view of an alternative embodiment of a vial adapter comprising a conduit tip.
Figure 9B:
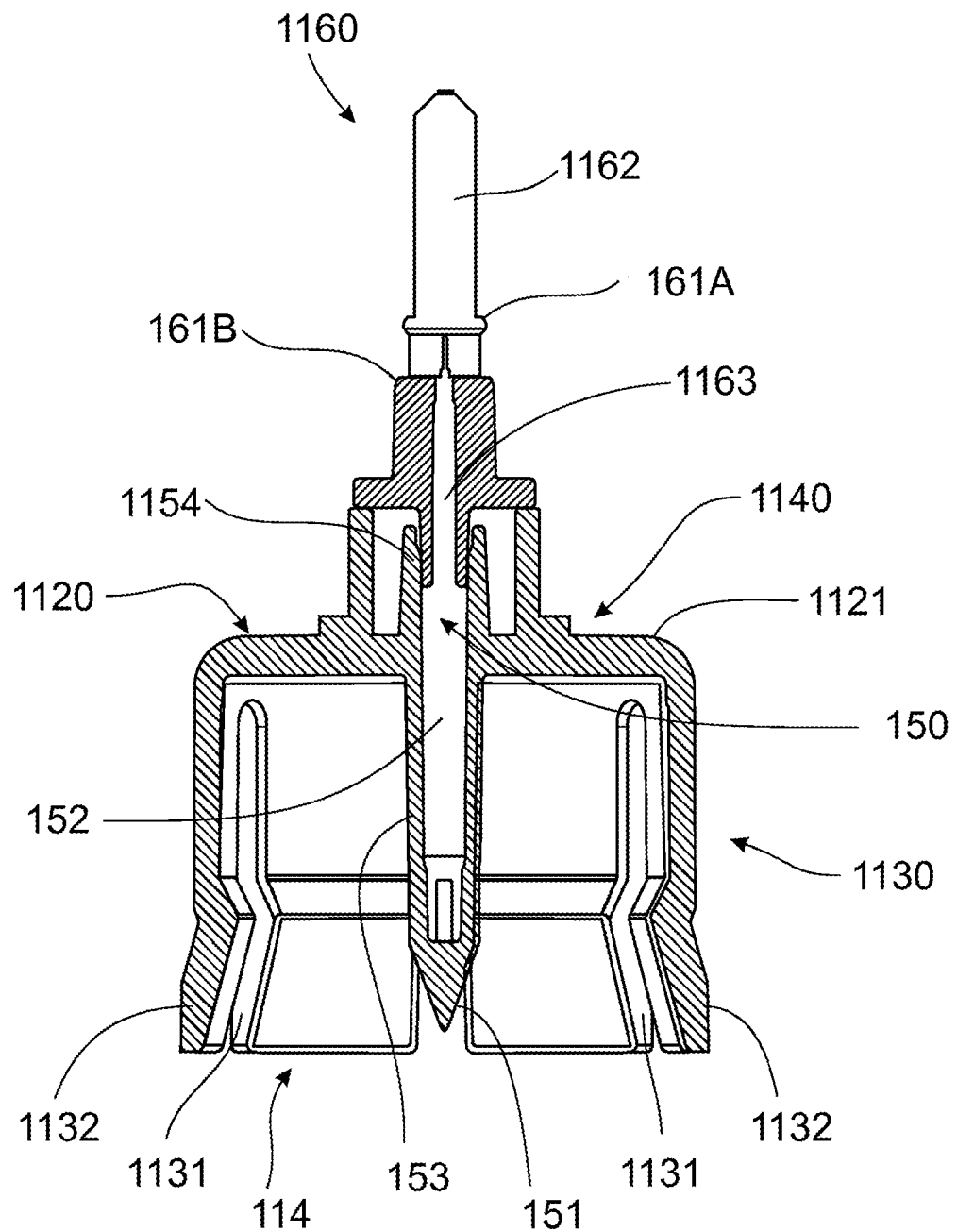
FIG. 9B is a sectional view of the embodiment shown in FIG. 9A.

An alternative embodiment of vial adapter 1100 is shown in FIGS. 8A and 8B. FIG. 9A is an isometric view of vial adapter 1100 and FIG. 8B is a sectional view of adapter 1100. Adapter 1100 comprises housing 1110 having shroud 1130 extending or projecting distally therefrom and conduit tip 1190 projecting from connector 1140 on outer surface 1121 of base 1121, essentially as hereinbefore described. Conduit tip 1160 comprises projection 1162 and internal bore 1163 which permits fluid flow between a fluid delivery device, such as syringe 400 shown in FIG. 8, and a vial closure without risk of premature safety activation, as hereinbefore described. In this embodiment, housing 1120 of vial adapter 1100 comprises shroud 1130 comprising a plurality of longitudinal slits 1131 and longitudinal arms 1132. While longitudinal arms 1132 are capable of elastic deformation to thereby engage or capture a vial closure (or a crimped metal retainer fitted to the vial closure), this embodiment is more suited to vials of a particular size (e.g., diameter) or relatively narrow range of sizes while providing the conduit tip 1160 to prevent or avoid premature activation of syringe safety mechanisms.

It will be appreciated that conduit tip, cannula, base and shroud, connection port, and other components of the vial adapter may be separate or unified components which provide multiple functions. For example and as described previously, the conduit tip and cannula may be separate or a unified, integrally-formed component that functions to prevent retraction activation, the cannula to pierce the sealing membrane of the vial closure and provide a fluid conduit between the fluid container or fluid conduction device and the vial closure. The unified conduit tip and cannula may also be attached to the connector and/or the base and shroud of the vial adapters. In at least one embodiment described in, conduit tip is a separate component attached to the remaining components of vial adapter. In another embodiment the cannula and the connection port are pre-formed aspects on opposing surfaces of base, from which the shroud also extends; while the tip is a separate component connected to the connection port. A range of assembly configurations can be achieved with the components of the vial adapters described herein. Such configurations provide various manufacturing and assembly advantages, and can be adjusted to meet a range of needs while providing the same general functionality of the resulting vial adapters.

Figure 10:
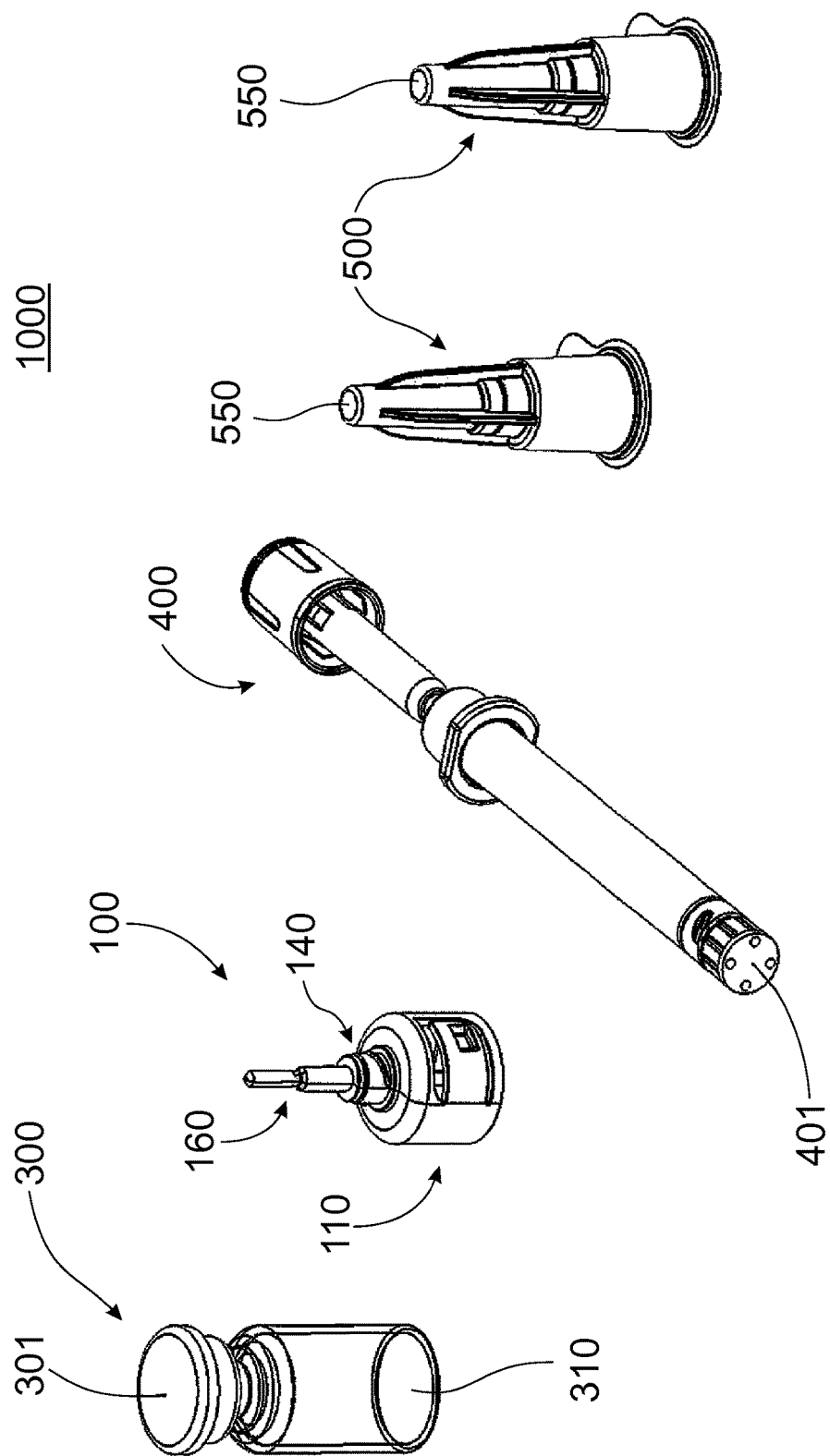
FIG. 10 shows an isometric view of a kit for drug storage, preparation, and/or delivery which includes a vial adapter.

Other embodiments provide a kit 1000 which may comprise one or more vial adapters 100 wherein vial adapter 100 is fully assembled or where one or more vial adapters are provided with separate components to be assembled by the user, such as hereinbefore described and shown in FIG. 10. Kits 1000 may further comprise a syringe such as retractable syringe 400 and one or more retractable needle assemblies 500 either as fully assembled or separate components (e.g., separate barrel, needle assembly, and plunger components). The kits 1000 may further comprise a vial 300. The vial 300 may have container 310 and a vial seal, such as elastomeric, permeable vial seal 301, that may be pierced by the vial adapter 100. The syringe 400 may also have an elastomeric seal, such as tip cap 401, that may be removed to connect syringe 400 to vial adapter 100 at connector 140 of vial adapter 100. The vial adapter thus facilitates a connection between the vial and the syringe to permit fluid flow, such as through the conduit tip 160. Some syringes 400, particularly non-retractable syringes, may utilize a vial adapter that does not require the conduit tip 160 shown in FIG. 10, or a conduit tip 160 at all (as shown in FIGS. 2A and 2B). After fluid transfer from the vial 300 to the syringe 400, vial adapter 100 may be disconnected and a needle assembly, such as a retractable needle assembly 500, may be attached to the syringe 400 for drug delivery to a user. The needle assemblies 500 shown in FIG. 10 are enclosed in needle cap 550.

Figure 11:
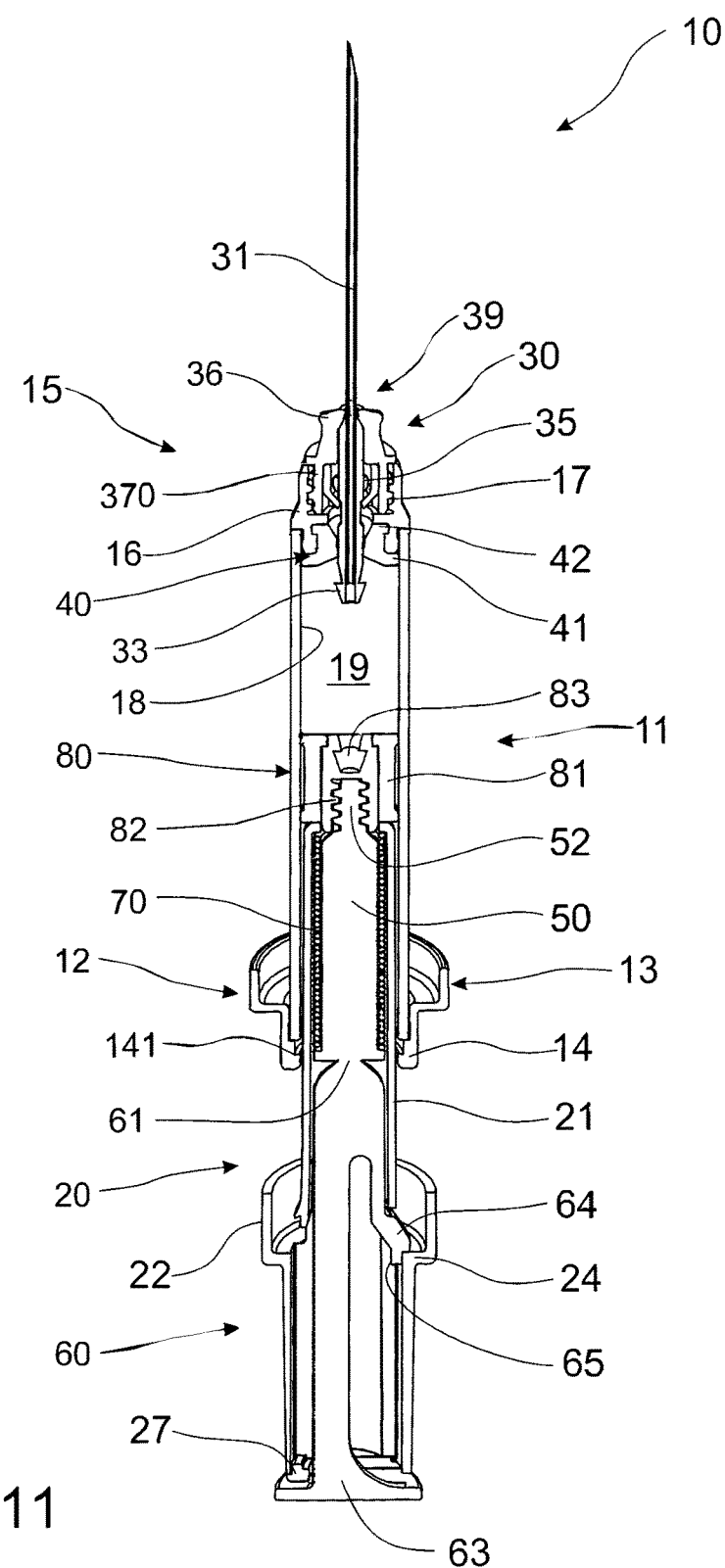
FIG. 11 is a sectional view of an embodiment of a retractable syringe.

Referring to FIG. 11, an embodiment of syringe 10 comprises barrel 11 and plunger 20 which is slidably, axially moveable within barrel 11, plunger 20 having plunger member 50 and plunger housing 21. Replaceable needle assembly 30 comprises retractable needle 39 that comprises cannula 31 and needle body 32 comprising plunger-engaging foot 33, needle mount 36 having screw threaded portion 370 and needle retainer 35. Seal 80 is mounted to projection 52 of plunger member 50. Barrel 11 comprises plunger end 12 at which is located collar 13 comprising release ring 14 having rim 141. Barrel 11 also comprises needle end 15 having mounting member 16 onto which can be mounted replaceable needle assembly 30. Mounting member 16 comprises screw thread 17 and is typically glued or otherwise firmly affixed inside needle end 15 of barrel 11. Needle seal 40 is also mounted inside needle end 15 of barrel 11 behind mounting member 16 (i.e proximal to the user). Sealing base 41 of needle seal 40 seals against inside wall 18 of barrel while body 42 is coupled to mounting member 16.

Figure 12:
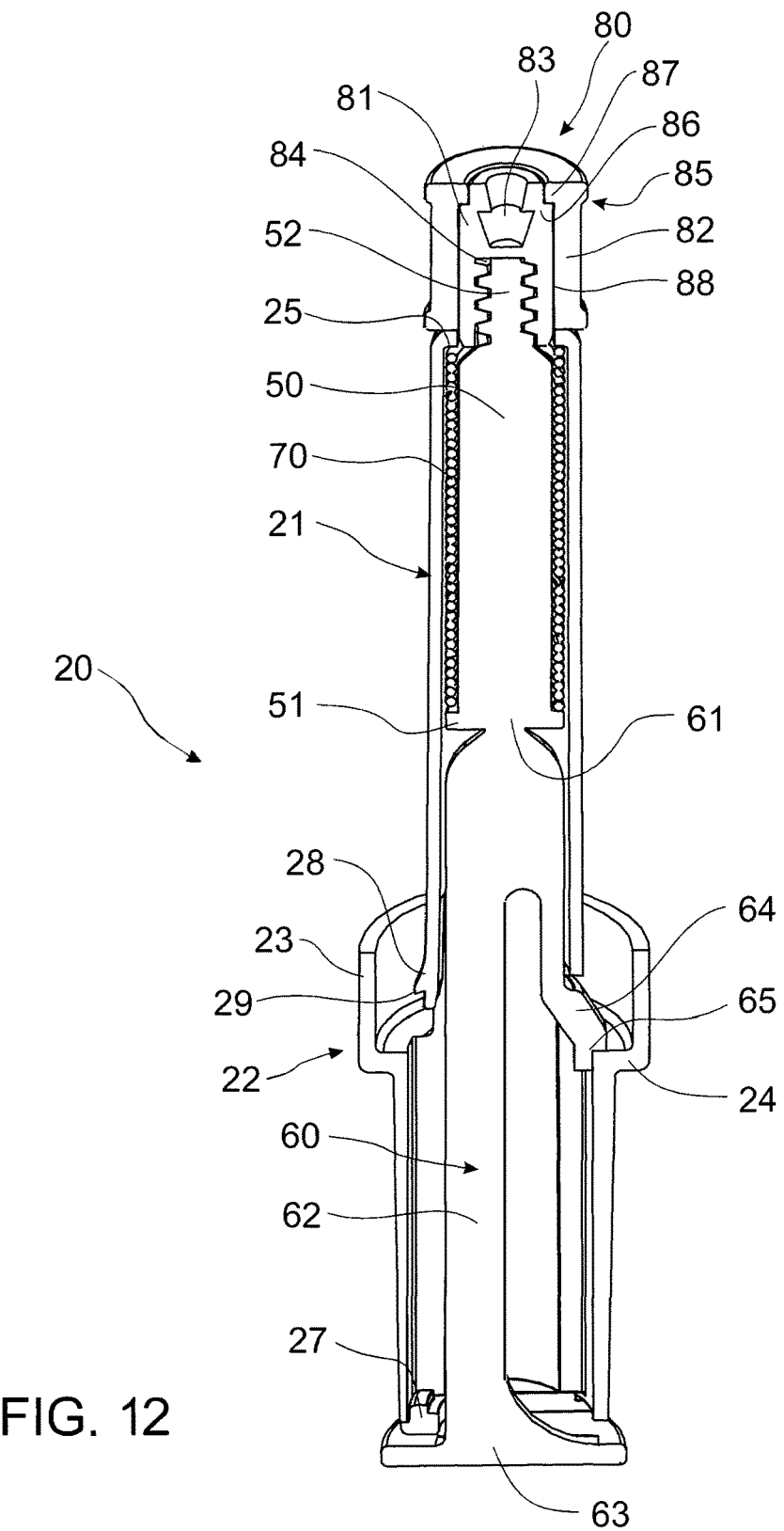
FIG. 12 is a sectional view of an embodiment of a plunger.

Referring now to FIG. 12, plunger 20 comprises plunger housing 21 with skirt 22 having flange 23 comprising inner circumferential ledge 24. Skirt 22 also comprises step 27 at an end of skirt 22 proximal to a user. Plunger housing 21 further comprises arm 28 having shoulder 29. Control rod 60 is releasably connected to plunger member 50 by way of frangible connection 61. Control rod further comprises shaft 62, button 63 which is operable by a user and trigger 64 which comprises notch 65. In this embodiment, the biasing means is spring 70. Before retraction, trigger 64 of control rod 60 engages flange 23 of plunger housing 21 by way of notch 65 releasably engaging inner circumferential ledge 24. This retains 5 spring 70 in an initially compressed state, compressed between inner shoulder 25 of plunger housing and annular base 51 of plunger member 50. In this context, "initially compressed" means that spring 70 is in a compressed (i.e energized) state before use of the retractable syringe.

Plunger member 50 further comprises projection 52, which in this embodiment is screw threaded, which is coupled to plunger seal 80. Plunger seal 80 comprises inner member 81 and outer member 82 that are releasably coupled. Stop 85 is formed between shoulder 86 of inner member 81 and ledge 87 of outer member 82 to minimize or prevent unwanted forward travel of inner member 81 relative to outer member 82 (i.e towards needle end 15 of barrel 11), particularly when plunger 20 is initially inserted into barrel 10. Stop 85 selectively allows axial movement of inner member 81 relative to outer member 82 towards the user during retraction, as will be described in more detail hereinafter. Inner member 81 further comprises complementary mating portion 83 for receiving and engaging foot 33 of needle body 32 and plunger-engaging recess 84 that is screw-threadedly mounted to projection 52 of plunger member 50. Outer member 82 seals against inside wall 18 of barrel to prevent fluid leaking from fluid space 19. It is also noted that inner member 81 and outer member 82 provide a fluid-tight seal at internal interface 88. Although not shown, complementary annular ribs and grooves could be added to inner member 81 and outer member 82, or vice versa, to facilitate the fluid-tight seal.

Figure 13:
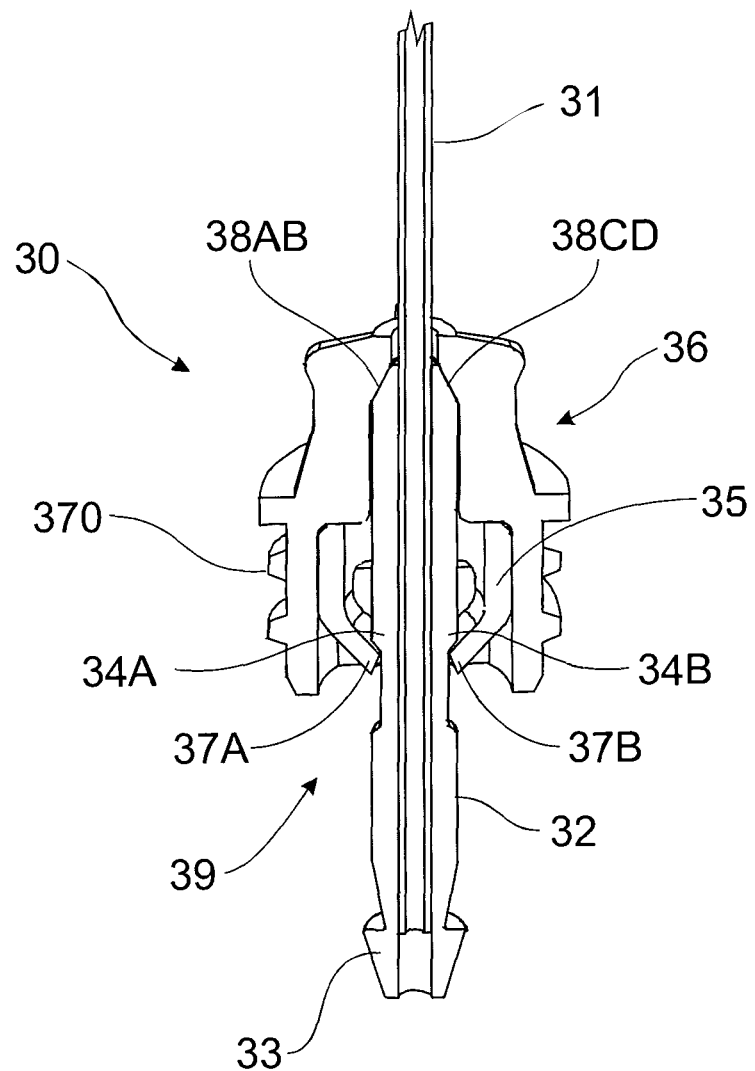
FIG. 13 is a sectional view of an embodiment of a replaceable needle assembly.

As shown in FIG. 13, replaceable needle assembly 30 comprises retractable needle 39 comprising cannula 31, needle body 32 that comprises plunger-engaging foot 33 and shoulders 34A, 34B, needle retainer 35 and needle mount 36 having screw threaded "male" portion 370. Needle retainer 35 also comprises fingers 37A, B that respectively bear against shoulders 34A, 34B of needle body 32 which retain retractable needle 39 in needle assembly 30 and prevent inadvertent retraction of retractable needle 39. This retaining function can withstand up to a 6N force, but nevertheless allow spring-driven retraction of retractable needle 39, as will be described in more detail hereinafter. An advantage of this arrangement is that no other structure (e.g. an ejector member) is required to release retractable needle 39 from fingers 37A, 37B. Complementary angled faces 38A, B, C 5 and D also assist preventing inadvertent ejection of retractable needle, if for example subjected to a "needle pull" force 39 from needle assembly 30.

Figures 14A, 14B:
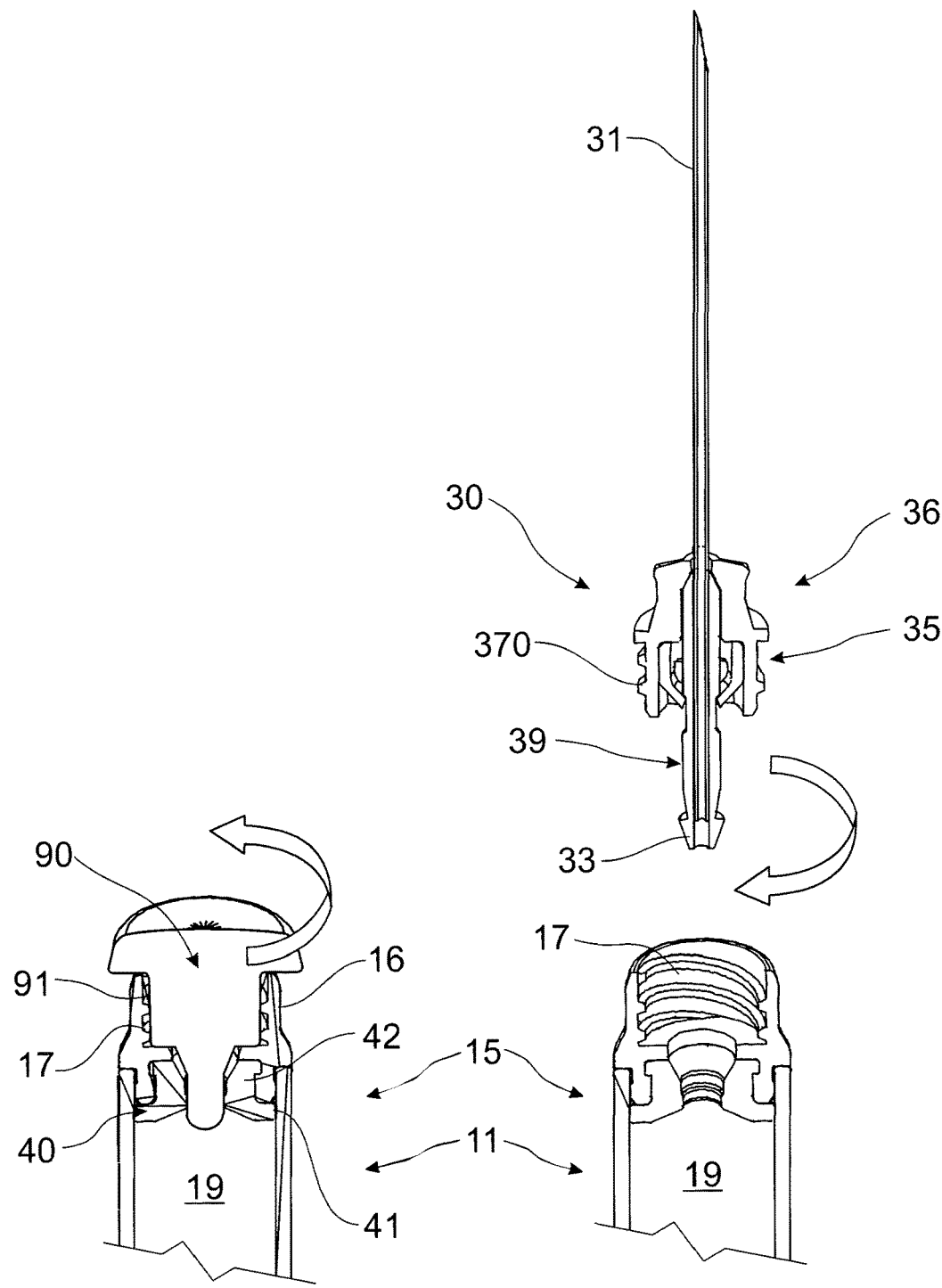
FIG. 14A is a sectional view of an embodiment of a barrel prior to removal of a plug and FIG. 14B is a sectional view showing mounting of a replaceable needle assembly to a barrel mounting member.

Referring now to FIGS. 14A and 14B, syringe 10 is typically provided prefilled with fluid contents, such as a vaccine, although without limitation thereto. As is evident in FIG. 14A, prior to use, plug 90 comprising screw-threaded portion 91 has been fitted into complementary screw-thread 17 of mounting member 16 at needle end 15 of barrel 11 to thereby seal barrel 11. Plug 90 is then unscrewed as indicated by the arrow and removed by the user so that replaceable needle assembly 30 can be mounted by way of screw thread 35 in needle mount 36 engaging complementary screw thread 17 in mounting member 16. Replaceable needle assembly 30 may be provided with a removable cover (not shown) for cannula 31 and also a screwthreaded cover (not shown) mountable to screw thread 35 of needle mount 36. Once these covers are removed and the needle assembly mounted to barrel 11, syringe 10 is ready for use. It will be appreciated that the replaceable needle assembly 30 allows a user to replace a needle that becomes bent or burred. Furthermore, a user may select an appropriate size or gauge needle for delivery.

Figure 15:
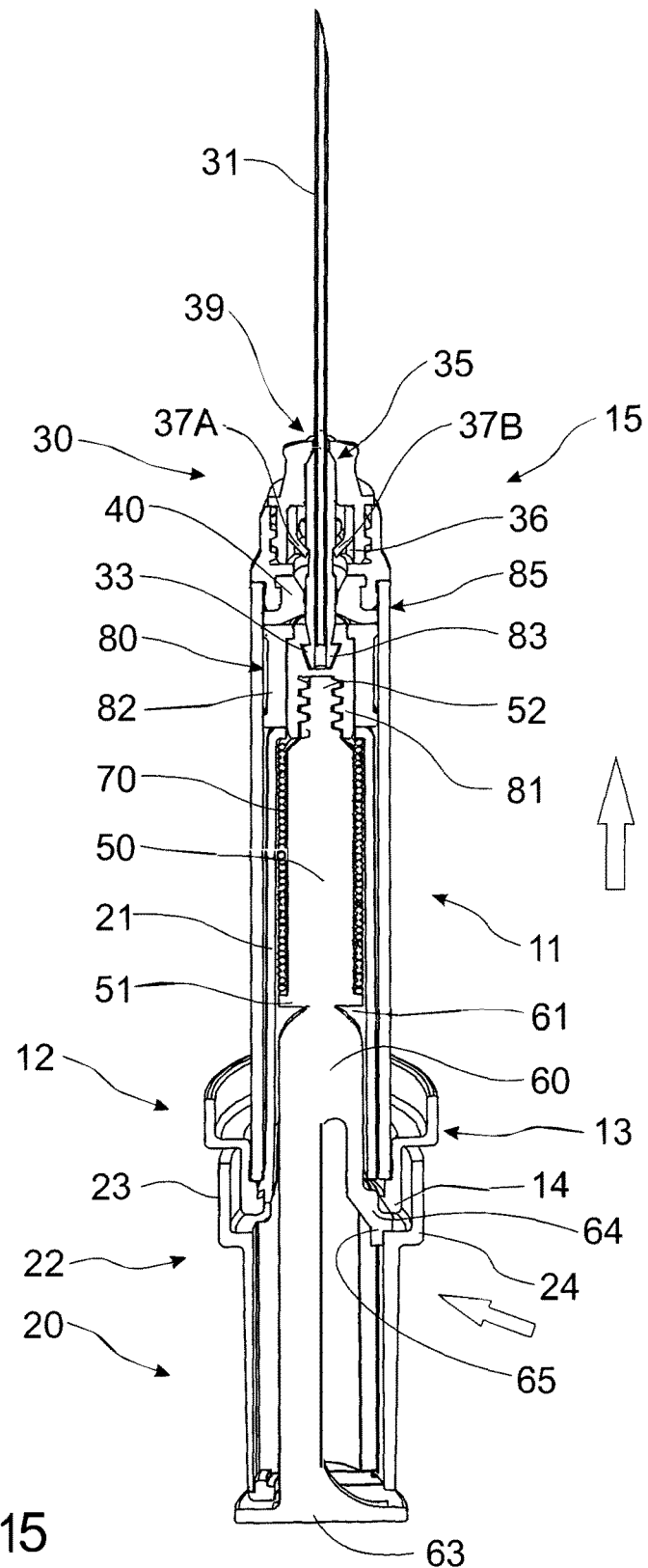
FIG. 15 is a sectional view of a plunger engaging a needle assembly prior to needle retraction.

Referring to FIG. 15, in use plunger 20 is moved axially in the direction of the solid arrow toward needle end 15 of barrel 11 to deliver fluid contents of syringe 10. At or near the end of plunger 20 depression, complementary mating portion 83 of seal inner 81 receives and snap-lock engages foot 33 of needle body 32. This effectively couples retractable needle 39 to plunger member 50, as shown in FIG. 15. It will also be appreciated that while this embodiment describes male-female engagement between foot 33 and complementary mating portion 83, the reverse arrangement is also contemplated. The sequence of events that occur to facilitate controlled retraction of retractable needle 39 is as follows.

Continued movement of plunger 20 in the direction of the solid arrow in FIG. 15 is allowed by seal 80 and needle seal 40, which are formed of a compressible material and allow continued movement of plunger housing 21 toward needle end 15 of barrel 11 until release ring 14 bears against arm 64 of control rod 60, thereby moving trigger 64 radially inwardly in the direction of the arrow in FIG. 15. This disengages notch 65 from inner circumferential ledge 24 which thereby triggers release of control rod 60 from plunger housing 21. This allows initially compressed spring 70 to decompress and forcibly bear against annular base 51 of plunger member 50 to thereby retract plunger member 50 and connected control rod 60. Retraction of plunger member 50 occurs with sufficient force to dislodge needle body 32 from fingers 37A, B of needle retainer 35. At this time, inner member 81 of plunger seal 80 uncouples from outer member 82, moving axially towards the user so that cannula 31 and needle body 32, which is coupled to inner sealing member 81 mounted to plunger member 50, retracts in the direction of the arrow in FIG. 16 (inside plunger housing 21 which remains stationary relative to barrel 11).

Figure 17:
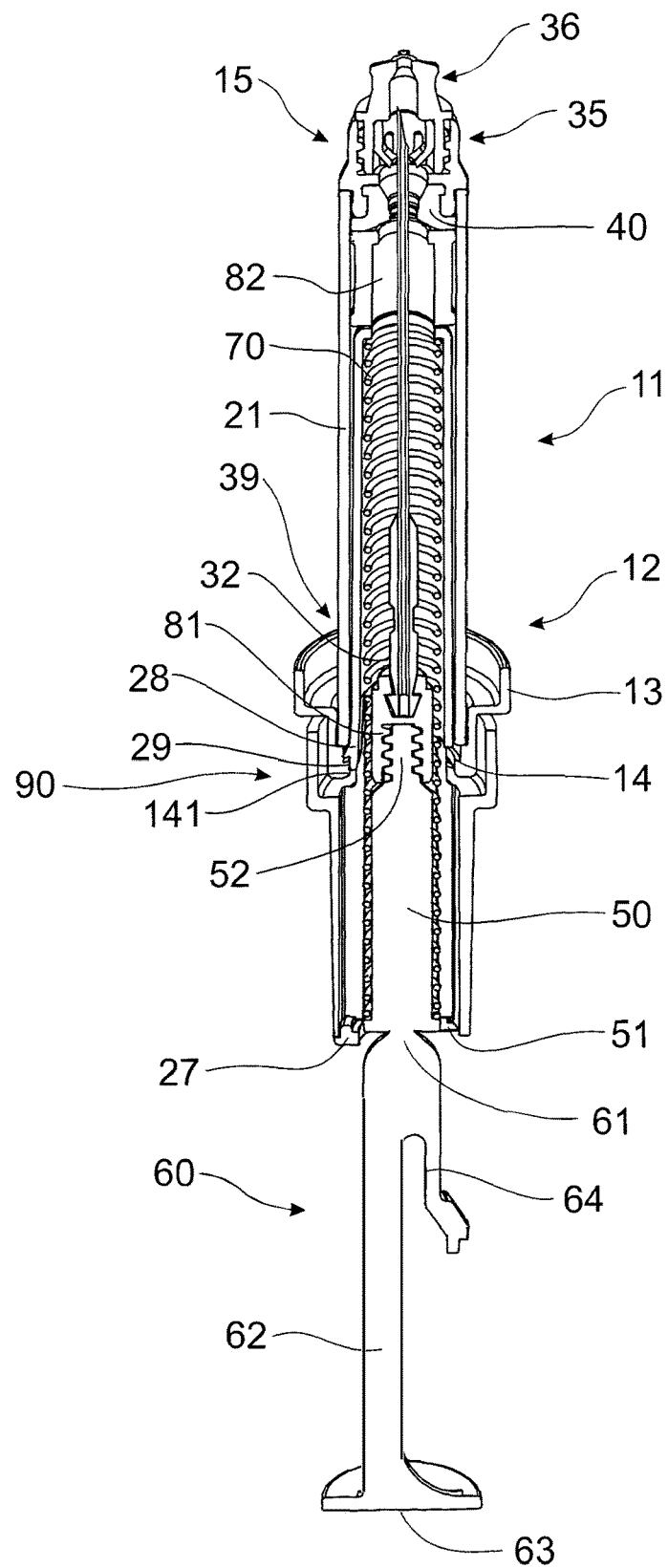
FIG. 17 is a sectional view showing an embodiment of a retractable syringe after retraction of a retractable needle.

Accordingly, control rod 60 retracts, the rate of which retraction is controlled by a user relaxing pressure (such as by way of thumb pressure) against control button 63. As shown in FIG. 17, retraction is complete when base 51 of first plunger member 50 abuts step 27 in plunger housing 21 which is stationary during retraction of plunger member 50 and control rod 60. Needle seal 40, needle mount 36 and needle retainer 35 also remain stationary at needle end 15 of barrel 11.

Figure 16:
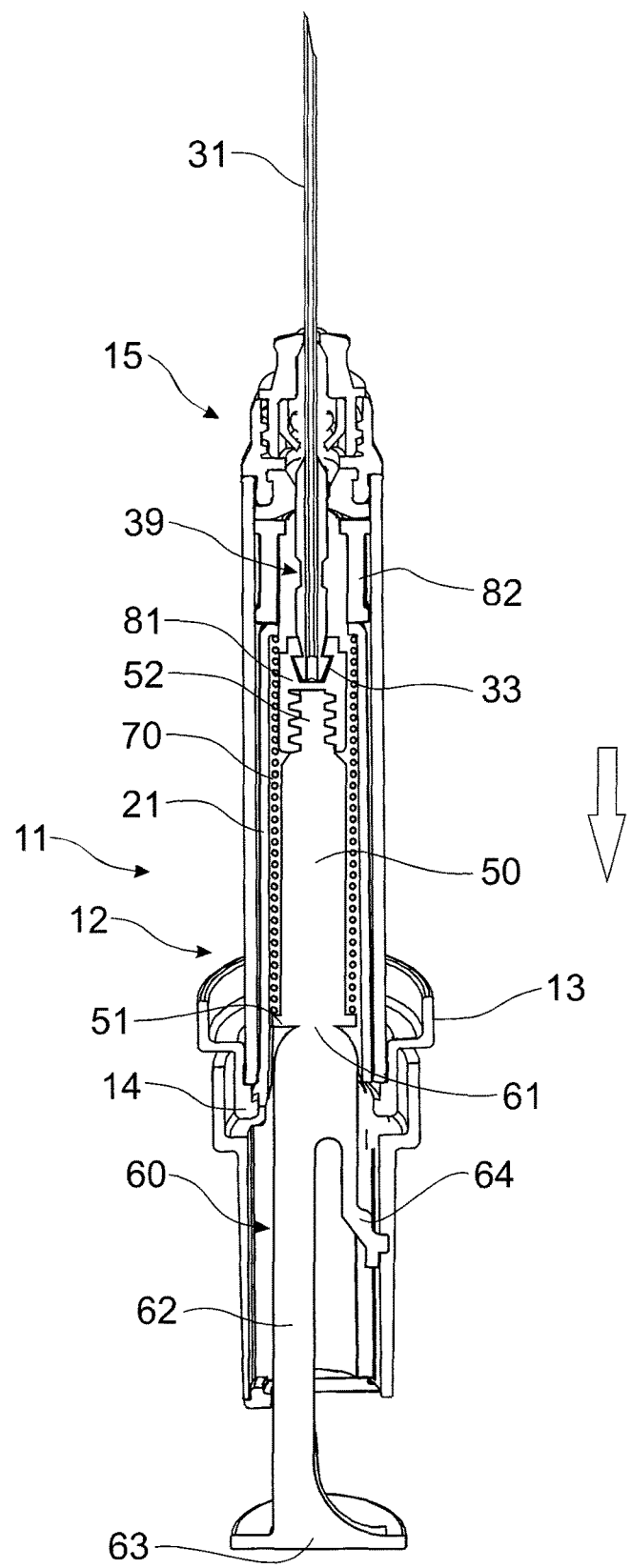
FIG. 16 is a sectional view showing spring-driven retraction of a plunger, plunger rod and retractable needle.

As shown in FIGS. 16 and 17, at the end of plunger 20 depression to complete injection of fluid contents of syringe 10, lock 90 is formed between lock elements in the form of shoulder 29 of arm 28 of plunger housing 21 locked onto rim 141 inside release ring 14 of collar 13 at plunger end 12 of barrel 11, to thereby prevent withdrawal of plunger housing 21 from barrel 11. This also facilitates ease of removal of control rod 60, which can be manually removed from syringe 10 by breaking control rod 60 away from plunger member 50 at frangible connection 61. Control rod 60 may then be discarded as "clean" waste, leaving syringe 10 with plunger housing 21 and plunger member 50 remaining inside barrel 11 for a more compact medical waste disposal.

It will be appreciated that the foregoing description provides examples of the disclosed vial adapter and method of use. However, it is contemplated that other embodiments or implementations may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A method of transferring fluid from a vial comprising a closure to a safety syringe, said method including connecting a vial adapter to the closure of the vial and to the safety syringe, fitting lateral arms of the vial adapter to the closure so that the vial adapter is in fluid communication with said safety syringe and inserting a conduit tip of the vial adapter into the safety syringe, the conduit tip inhibiting travel of a plunger of the safety syringe towards a distal end of the safety syringe.

2. The method of claim 1, further including transferring fluid from the vial to the safety syringe.

3. A vial adapter for interconnecting a safety syringe and a vial comprising a closure having a seal, said vial adapter comprising an adapter housing having a base, a shroud extending or projecting from the base which is capable of releasably engaging the vial closure, a cannula extending or projecting from the base for penetrating said seal to thereby establish fluid communication between the vial and the vial adapter and a conduit tip which inhibits travel of a plunger of the safety syringe towards a distal end of the safety syringe.

4. The vial adapter of claim 3, wherein the conduit tip projects or extends from the connector.

5. The vial adapter of claim 4, wherein the conduit tip projects or extends proximally from the connector.

6. The vial adapter of claim 3, wherein the conduit tip is attachable to the connector.

7. The vial adapter of claim 3, wherein the conduit tip is integrally formed or unitary with the connector.

8. The vial adapter of claim 3, wherein the conduit tip comprises at least one internal aperture that permits fluid flow through the conduit tip.

9. The vial adapter of claim 8, wherein at least part of the cannula is in fluid communication with the conduit tip to thereby allow fluid communication between the vial, the cannula and the conduit tip.

10. The vial adapter of claim 3, wherein the shroud further comprises at least one latitudinal aperture within which resides a flexion arm connected at one end to the shroud.

11. The vial adapter of claim 10, wherein the flexion arm is configured to engage the vial adapter on the vial closure.

12. The vial adapter of claim 11, wherein the flexion arm comprises a gripping aspect.

13. The vial adapter of claim 3, wherein the shroud comprises at least one longitudinal slit, wherein at least one longitudinal arm resides between adjacent slits, respectively, each connected at one end to the shroud.

14. The vial adapter of claim 13, wherein the at least one longitudinal arm is configured to engage the vial adapter on the vial closure.

15. The vial adapter of claim 14, wherein the at least one longitudinal arm is deformable.

16. A kit comprising at least one vial adapter according to claim 3 and the safety syringe or individual components thereof.

17. The kit of claim 16, wherein the safety syringe comprises a replaceable retractable needle.

18. The kit of claim 17, which further comprises a plurality of replaceable, retractable needles.

* * * * *